US006399859B1

United States Patent
Nichols et al.

(10) Patent No.: US 6,399,859 B1
(45) Date of Patent: Jun. 4, 2002

(54) PLANT URIDINE DIPHOSPHATE-GLUCOSE DEHYDROGENASE GENES, PROTEINS, AND USES THEREOF

(75) Inventors: Scott E. Nichols; Kanwarpal S. Dhugga, both of Johnston; George W. Singletary, Ankeny; Court A. Saunders, Clive, all of IA (US); Derrick Witcher, Fishers, IN (US); Wesley B. Bruce, Urbandale, IA (US); Lynne E. Sims, Polk City, IA (US); Guihua Lu; Gan-Yuan Zhong, both of Urbandale, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 08/987,367

(22) Filed: Dec. 10, 1997

(51) Int. Cl.[7] .......................... C12N 15/82; C12N 5/04; C12N 15/29; A01H 5/00
(52) U.S. Cl. .................... 800/298; 800/295; 800/300.1; 800/317.2; 800/320.1; 800/320.2; 800/320.3; 435/412; 435/417; 435/418; 435/419; 435/255.1; 435/25.7; 435/320.1; 435/410; 536/23.1; 536/23.2; 536/23.6
(58) Field of Search ............................. 536/23.6, 23.1, 536/23.2; 800/278, 284, 279, 295, 298, 300.1, 317.2, 320, 320.1, 320.2, 320.3; 435/410, 412, 417, 418, 419, 255.1, 257.1, 320.1

(56) References Cited

FOREIGN PATENT DOCUMENTS

WO   WO 99/23200   5/1999

OTHER PUBLICATIONS

Neuhaus et al. Plant Molecular Biology. 1991. vol. 16: 141–151.*
Kossmann et al. Progress in Biotechnology–10. Meeting was held from Apr. 23 to Apr. 26, 1995, 1991.*
Roche et al. Plant Molecular Biology. 1993. vol. 22: 971–983.*
Napoli et al. 1989. The Plant Cell. vol. 2: 278–289.*
Carvalho et al. The EMBO J. 1992. vol. 11, 2595–2602.*
Robertson et al. Biochem J. 1996. vol. 313: 311–317.*
Ausbel et al. Short Protocolas in Molecular Biology. 1989.*
Spencer et al. Plant Molecular Biology. 1992. vol. 18: 201–210.*
Covitz et al. "00755 MtRHE Medicago truncatula cDNA 5' similar to UDP–glucose dehydrogenase", *EMBL Accession No. AA660860*, Nov. 14, 1997 (XP002104089).
Tenhaken et al., "Cloning of an Enzyme that Synthesizes a Key Nucleotide–Sugar Precursor of Hemicellulose Biosynthesis for Soybean: UDP–Glucose Dehydrogenase", *Plant Physiology* 12:1127–1134, 1996 (XP002104090).
Carson et al., "EST162 Sugarcane leaf roll Saccharum sp. CDNA clone E37–rev similar to UDP–glucose dehydrogenase" *EMBL Accession No. AA525658*, Jul. 22, 1997 (XP002104091).
Sasaki et al., "Rice cDNA, partial sequence (E0489_IA)", *EMBL Accession No. C71864*, Sep. 19, 1997 (XP002104092).
Newman et al., "10058 Lambda–PRL2 *Arabidopsis thaliana* cDNA clone 143K15T7, mRNA sequence", EMBL Accession No. T46795, Feb. 11, 1995 (XP002104093).
Newman et al., "14790 Lambda–PRL2 *Arabidopsis thaliana* cDNA clone 176P16T7", EMBL Accession No. H36268, Jul. 26, 1995 (XP002104094).
Newman et al., "12856 Lambda–PRL2 *Arabidopsis thaliana* cDNA clone 159B10T7", EMBL Accession No. R30251, Oct. 11, 1995 (XP002104095).
Newman et al., "17408 Lambda–PRL2 *Arabidopsis thaliana* cDNA clone 200L6T7", EMBL Accession No. H76977, Aug. 11, 1995 (XP002104096).
Nakamura, Y., "*Arabidopsis Thaliana* genomic DNA, chromosome 5, TAC clone: K3K3", EMBL Accession No. AB010694, Feb. 3, 1998 (XP002104097).
Hempel et al., "UDP–glucose dehydrogenase from bovine liver: Primary structure and relationship to other dehydrogenases", *Protein Science* 3:1074–1080. 1994

* cited by examiner

*Primary Examiner*—Amy J. Nelson
*Assistant Examiner*—Ousama Zaghmout
(74) *Attorney, Agent, or Firm*—Pioneer Hi-Bred International, Inc.

(57) ABSTRACT

Isolated nucleic acid molecules are provided that encode maize UDPGdH variant UDPGdH, and mutant UDPGdH proteins. These nucleic acid molecules can be used to produce transgenic plants having altered quality or quantity of starch. Also provided are vectors capable of expressing such nucleic acid molecules, host cells containing, such vectors, and polypeptides encoded by such nucleic acids.

11 Claims, 4 Drawing Sheets

| | | | | | |
|---|---|---|---|---|---|
|    1 | CACAAACACA | AGTCGTCGTA | GGCAGCGAGC | GTCTCTCCTC | TCCCACGCAT |
|   51 | CGCGCCAAGG | AAGAGAGAGA | GATCGCCGCT | CCCCTTCTCG | GCGTCGGTGG |
|  101 | TGCGGGTGCC | CTCCCTCCTC | GAGCGAGATC | TGTCTGGTCA | CAGATCTATC |
|  151 | TGACAAAATG | GTGAAGATCT | GCTGCATCGG | TGCTGGCTAT | GTCGGTGGCC |
|  201 | CAACCATGGC | CGTCATTGCC | CTCAAGTGCC | CAGACATTGA | GGTCGTCGTC |
|  251 | GTTGACATCT | CCAAGCCCCG | CATTGAGGCC | TGGAACAGTG | ACACCCTGCC |
|  301 | AATCTACGAG | CCTGGTCTCG | ATGATGTTGT | GAAGCAGTGC | AGGGGCAGGA |
|  351 | ACCTCTTCTT | CAGCACTGAT | GTTGAGAAGC | ACGTCGCTGA | GGCTGACATT |
|  401 | ATCTTTGTCT | CGGTGAACAC | CCCCACCAAG | ACCCGTGGGC | TTGGAGCTGG |
|  451 | CAAGGCTGCC | GACCTCACCT | ACTGGGAGAG | CGCTGCCCGC | ATGATTGCGG |
|  501 | ATGTCTCCAA | GTCTGACAAG | ATTGTTGTTG | AGAAGTCCAC | TGTCCCTGTC |
|  651 | AAGACCGCTG | AGGCTATTGA | GAAGATCTTG | ACCCACAACA | GCAAGGGCAT |
|  601 | CAACTACCAG | ATCCTTTCCA | ACCCAGAGTT | CCTTGCGGAG | GGCACTGCCA |
|  651 | TTGAGGACCT | GTTCAAGCCT | GACAGAGTGC | TTATCGGTGG | CCGGGAGACC |
|  701 | CCTGAGGGCA | GGAAGGCCGT | CCAGGCTCTC | AAGGATGTGT | ACGCTCACTG |
|  751 | GGTTCCCGAG | GACAGGATCC | TCACCACCAA | CCTGTGGTCT | GCTGAGCTCT |
|  801 | CCAAGCTCGC | TGCCAACGCG | TTCCTGGCAC | AGAGGATCTC | CTCTGTGAAC |
|  851 | GCCATCTCCG | CCCTCTGCGA | GGCCACCGGC | GCGAATGTGA | CTGAGGTGGC |
|  901 | TTACGCCGTG | GGCAAGGACA | CGAGGATTGG | CCCCAAGTTC | CTGAACGCCA |
|  951 | GTGTTGGGTT | CGGTGGGTCT | TGCTTCCAGA | AGGACATCCT | GAACCTGGTG |
| 1001 | TACATCTGCG | AGTGCAATGG | CCTGCCCGAG | GTGGCCAACT | ACTGGAAGCA |
| 1051 | GGTGATCAAG | ATCAACGACT | ACCAGAAGAG | CCGGTTCGTG | AACCGCGTCG |
| 1101 | TGTCGTCCAT | GTTCAACACC | GTTGCCGGCA | AAAAGATCGC | CGTCCTCGGC |
| 1151 | TTCGCCTTCA | AGAAGGACAC | CGGCGACACC | AGGGAGACCC | CGGCCATCGA |
| 1201 | TGTCTGCAAG | GGCCTGCTGG | GTGACAAGGC | CCAGATCAGC | ATCTACGACC |
| 1251 | CCCAGGTGAC | GGAGGACCAG | ATCCAGCGGG | ACCTAGCCAT | GAACAAGTTC |
| 1301 | GACTGGGACC | ACCCGATGCA | CCTGCAGCCG | ACGAGCCCGA | CGGCCGTGAA |
| 1351 | GCAGGTGAGC | TGCGTGTGGG | ACGCGTACGA | GGCCACCAAG | GGCGCCCACG |
| 1401 | GGCTGTGCAT | CCTGACCGAG | TGGGACGAGT | TCAAGACCCT | GGACTACCAG |
| 1451 | AAGATCTTCG | ACAACATGCA | GAAGCCCGCC | TTCGTCTTCG | ACGGCCGCAA |
| 1501 | CATCGTCGAC | TCCGAGAAGC | TGAGGGAGAT | CGGCTTCATC | GTCTACTCCA |
| 1551 | TCGGCAAGCC | GCTCGACGCC | TGGCTCAAGG | ACATGCCCGC | GGTCGCCTAA |
| 1601 | TCCCACCCCC | CTCACCCATG | GATTGGATTC | CGGGAAGGAA | GAGGAGAGAA |
| 1651 | GCTGGTTGAC | CGTTCTTTAT | TACAGTTTGT | TTTTGCAGGC | TACGCTACCG |
| 1701 | ATTTTCTCTT | GTGTCAGGCA | TAAAAAAGG | TTGGACGGGC | TGCTAGTATT |
| 1751 | CCCTGCTGTT | TGGTGTTTTC | GTATCGGAGG | ACGTCTGTAG | ATGTACAATT |
| 1801 | CCTCAGGCCC | CTTGTGTTCG | GCTTGAGGAA | GTTTCCGTTG | TACCCTGGAC |
| 1851 | CTGCTATAGC | CGGTTGATTC | TTCAATTGTA | TTCCTAAAAG | TTACTAAAAA |
| 1901 | AAAAAAAAAA | AAAAAAAAAA | AAAACTCGAG | | |

FIGURE 1

```
  1  MVKICCIGAG  YVGGPTMAVI  ALKCPDIEVV  VVDISKPRIE  AWNSDTLPIY
 51  EPGLDDVVKQ  CRGRNLFFST  DVEKHVAEAD  IIFVSVNTPT  KTRGLGAGKA
101  ADLTYWESAA  RMIADVSKSD  KIVVEKSTVP  VKTAEAIEKI  LTHNSKGINY
151  QILSNPEFLA  EGTAIEDLFK  PDRVLIGGRE  TPEGRKAVQA  LKDVYAHWVP
201  EDRILTTNLW  SAELSKLAAN  AFLAQRISSV  NAISALCEAT  GANVTEVAYA
251  VGKDTRIGPK  FLNAIVGFGG  SCFQKDILNL  VYICECNGLP  EVANYWKQVI
301  KINDYQKSRF  VNRVVSSMFN  TVAGKKIAVL  GFAFKKDTGD  TRETPAIDVC
351  KGLLGDKAQI  SIYDPQVTED  QIQRDLAMNK  FDWDHPMHLQ  PTSPTAVKQV
401  SCVWDAYEAT  KGAHGLCILT  EWDEFKTLDY  QKIFDNMQKP  AFVFDGRNIV
451  DSEKLREIGF  IVYSIGKPLD  AWLKDMPAVA
```

FIGURE 2

```
   1  CACAACTCGT  AGGCAGCGAG  CGTCTCTCCT  CTTCCTCTCC  CACGCACCGC
  51  GCCAAGGAAG  GCAGAGAGAG  ATCGCCGCTC  CTCTTCTCTC  CGTCGGTGGT
 101  GCGGTTGACC  GCCCTCCTCG  AGCGAGATCT  CGCTGCAGTC  CCTCGAGATC
 151  TGGTCACAGA  TCTATCCGAC  AAGATGGTGA  AGATCTGCTG  CATCGGTGCT
 201  GGCTATGTCG  GTGGCCCAAC  CATGGCTGTC  ATTGCCCTAA  AGTGCCCAGA
 251  CATTGAGGTT  GTCGTTGTTG  ACATCTCCAA  GCCCCGCATT  GAGGCATGGA
 301  ACAGCGACAC  CCTCCCGATC  TACGAGCCCG  GCCTCGATGA  TGTTGTGAAG
 351  CAGTGCAGGG  GCAGGAACCT  CTTCTTCAGC  ACTGATGTTG  AGAAGCACGT
 401  CGCTGAGGCT  GACATCATCT  TCGTCTCGGT  GAACACCCCC  ACCAAGACCC
 451  GTGGGCTTGG  AGCTGGCAAG  GCTGCCGACC  TCACCTACTG  GGAGAGCGCT
 501  GCTCGTATGA  TCGCCGATGT  CTCCAAGTCT  GACAAGATCG  TTGTCGAGAA
 551  GTCCACCGTC  CCTGTCAAGA  CCGCTGAGGC  TATTGAGAAG  ATCTTGACCC
 601  ACAACAGCAA  GGGCATCAAC  TACCAGATCC  TTTCCAACCC  GGAGTTCCTT
 651  GCAGAGGGCA  CTGCTATTGA  GGACCTGTTC  AAGCCTGACA  GAGTGCTCAT
 701  CGGTGGCCGG  GAGACCCCCG  AGGGCAGGAA  AGCCGTCCAG  GTTCTCAAGG
 751  ATGTGTATGC  TCACTGGGTT  CCCGAGGACA  GGATCCTCAC  CACCAACCTG
 801  TGGTCCGCTG  AGCTCTCCAA  GCTCGCCGCC  AATGCGTTCT  GGCACAGAG
 851  GATCTCCTCT  GTCAATGCCA  TCTCCGCTCT  CTGCGAGGCA  ACCGGAGCCA
 901  ATGTCTCTGA  GGTGGCTTAC  GCCGTGGGCA  AGGACACGAG  AATTGGCCCC
 951  AAGTTCCTGA  ACGCCAGTGT  TGGGTTCGGT  GGCTCATGCT  TCCAGAAGGA
1001  CATCCTGAAC  CTGGTGTACA  TCTGCGAGTG  CAACGGCCTG  CCCGAGGTGG
1051  CCAACTACTG  GAAGCAGGTG  ATCAGGATCA  ACGACTACCA  GAAGAGCCGG
1101  TTCGTGAACC  GCGTCGTGGC  CTCCATGTTC  AACACCGTCG  CCGGCAAGAA
1151  GATCGCCGTC  CTCGGCTTCG  CCTTCAAGAA  AGACACCGGT  GACACCAGGG
1201  AGACCCCGGC  CATTGACGTC  TGCAAGGGCC  TGCTGGGCGA  CAAGGCCCAG
1251  ATCAGCATCT  ACGACCCCCA  GGTGACGGAG  GACCAGATCC  AGCGGGACCT
1301  GGCCATGAAC  AAGTTCGACT  GGGACCACCC  GATGCACCTG  CAACCGACGA
1351  GCCCCACGGC  CATTAAGCAG  GTGAGCTGCG  TGTGGGACGC  GTACGAGGCC
1401  ACCAAGGGCG  CCCACGGGGT  GTGCATCCTG  ACCGAGTGGG  ACGAGTTCAA
1451  GACCCTGGAC  TACCAGAAGA  TCTTCGACAA  CATGCAGAAG  CCCGCCTTCG
1501  TCTTCGACGG  CCGCAACATC  GTCGACCCGG  AGAAGCTGAG  GGAGATCGGC
1551  TTCATCGTCT  ACTCCATCGG  CAAGCCGCTC  GACGCCTGGC  TTAAGGACAT
1601  GCCCGCGGTC  GCTTAATTCG  TCTGAGGTGC  TCCATTGGAT  TGGATCCGGG
1651  GAAGGAAGAG  GAACTGGTTG  ACCATTCTTC  ATTACAGTTT  GTTTTTTGCA
1701  GGATTCTTAA  AAGTTGGACG  GCGCTGCTAG  TATTCCATGT  TTCGTGTTTT
1751  CATATTGGAG  GACGTCTGTA  GATGTAAAAA  ATCCTCGGGC  GCTTGTGCTC
1801  GGCTTGAGGA  AATATGCTTG  TACGGTTGTA  CCCTGGACCC  GCTATAGCTG
1851  GTTGGTTCTT  CAAGTTGTGT  TCCTATAGAA  GCCAAAGTTA  CTACACGATC
1901  GATATGTTCT  TTTTGCATAA  TAACAATACT  TGTCTCACGT  TTCATCC
```

FIGURE 3

```
  1  MVKICCIGAG  YVGGPTMAVI  ALKCPDIEVV  VVDISKPRIE  AWNSDTLPIY
 51  EPGLDDVVKQ  CRGRNLFFST  DVEKHVAEAD  IIFVSVNTPT  KTRGLGAGKA
101  ADLTYWESAA  RMIADVSKSD  KIVVEKSTVP  VKTAEAIEKI  LTHNSKGINY
151  QILSNPEFLA  EGTAIEDLFK  PDRVLIGGRE  TPEGRKAVQV  LKDVYAHWVP
201  EDRILTTNLW  SAELSKLAAN  AFLAQRISSV  NAISALCEAT  GANVSEVAYA
251  VGKDTRIGPK  FLNASVGFGG  SCFQKDILNL  VYICECNGLP  EVANYWKQVI
301  RINDYQKSRF  VNRVVASMFN  TVAGKKIAVL  GFAFKKDTGD  TRETPAIDVC
351  KGLLGDKAQI  SIYDPQVTED  QIQRDLAMNK  FDWDHPMHLQ  PTSPTAIKQV
401  SCVWDAYEAT  KGAHGVCILT  EWDEFKTLDY  QKIFDNMQKP  AFVFDGRNIV
451  DPEKLREIGF  IVYSIGKPLD  AWLKDMPAVA
```

FIGURE 4

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
         (A) LENGTH: 1930 base pairs
         (B) TYPE: nucleic acid
         (C) STRANDEDNESS: single
         (D) TOPOLOGY: linear (xi) SEQUENCE DESCRIPTION: SEQ ID NO:1:

```
CACAAACACA AGTCGTCGTA GGCAGCGAGC GTCTCTCCTC TCCCACGCAT CGCGCCAAGG      60

AAGAGAGAGA GATCGCCGCT CCCCTTCTCG GCGTCGGTGG TGCGGGTGCC CTCCCTCCTC     120

GAGCGAGATC TGTCTGGTCA CAGATCTATC TGACAAAATG GTGAAGATCT GCTGCATCGG     180

TGCTGGCTAT GTCGGTGGCC CAACCATGGC CGTCATTGCC CTCAAGTGCC CAGACATTGA     240

GGTCGTCGTC GTTGACATCT CCAAGCCCCG CATTGAGGCC TGGAACAGTG ACACCCTGCC     300

AATCTACGAG CCTGGTCTCG ATGATGTTGT GAAGCAGTGC AGGGGCAGGA ACCTCTTCTT     360

CAGCACTGAT GTTGAGAAGC ACGTCGCTGA GGCTGACATT ATCTTTGTCT CGGTGAACAC     420

CCCCACCAAG ACCCGTGGGC TTGGAGCTGG CAAGGCTGCC GACCTCACCT ACTGGGAGAG     480

CGCTGCCCGC ATGATTGCGG ATGTCTCCAA GTCTGACAAG ATTGTTGTTG AGAAGTCCAC     540

TGTCCCTGTC AAGACCGCTG AGGCTATTGA GAAGATCTTG ACCCACAACA GCAAGGGCAT     600

CAACTACCAG ATCCTTTCCA ACCCAGAGTT CCTTGCGGAG GGCACTGCCA TTGAGGACCT     660

GTTCAAGCCT GACAGAGTGC TTATCGGTGG CCGGGAGACC CCTGAGGGCA GGAAGGCCGT     720
```

-continued

```
CCAGGCTCTC AAGGATGTGT ACGCTCACTG GGTTCCCGAG GACAGGATCC TCACCACCAA      780

CCTGTGGTCT GCTGAGCTCT CCAAGCTCGC TGCCAACGCG TTCCTGGCAC AGAGGATCTC      840

CTCTGTGAAC GCCATCTCCG CCCTCTGCGA GGCCACCGGC GCGAATGTGA CTGAGGTGGC      900

TTACGCCGTG GGCAAGGACA CGAGGATTGG CCCCAAGTTC CTGAACGCCA GTGTTGGGTT      960

CGGTGGGTCT TGCTTCCAGA AGGACATCCT GAACCTGGTG TACATCTGCG AGTGCAATGG     1020

CCTGCCCGAG GTGGCCAACT ACTGGAAGCA GGTGATCAAG ATCAACGACT ACCAGAAGAG     1080

CCGGTTCGTG AACCGCGTCG TGTCGTCCAT GTTCAACACC GTTGCCGGCA AAAAGATCGC     1140

CGTCCTCGGC TTCGCCTTCA GAAGGACAC CGGCGACACC AGGGAGACCC CGGCCATCGA     1200

TGTCTGCAAG GGCCTGCTGG GTGACAAGGC CCAGATCAGC ATCTACGACC CCAGGTGAC     1260

GGAGGACCAG ATCCAGCGGG ACCTAGCCAT GAACAAGTTC GACTGGGACC ACCCGATGCA     1320

CCTGCAGCCG ACGAGCCCGA CGGCCGTGAA GCAGGTGAGC TGCGTGTGGG ACGCGTACGA     1380

GGCCACCAAG GGCGCCCACG GCTGTGCAT CCTGACCGAG TGGGACGAGT TCAAGACCCT     1440

GGACTACCAG AAGATCTTCG ACAACATGCA GAAGCCCGCC TTCGTCTTCG ACGGCCGCAA     1500

CATCGTCGAC TCCGAGAAGC TGAGGGAGAT CGGCTTCATC GTCTACTCCA TCGGCAAGCC     1560

GCTCGACGCC TGGCTCAAGG ACATGCCCGC GGTCGCCTAA TCCCACCCCC CTCACCCATG     1620

GATTGGATTC CGGGAAGGAA GAGGAGAGAA GCTGGTTGAC CGTTCTTTAT TACAGTTTGT     1680

TTTTGCAGGC TACGCTACCG ATTTTCTCTT GTGTCAGGCA TAAAAAAAGG TTGGACGGGC     1740

TGCTAGTATT CCCTGCTGTT TGGTGTTTTC GTATCGGAGG ACGTCTGTAG ATGTACAATT     1800

CCTCAGGCCC CTTGTGTTCG GCTTGAGGAA GTTTCCGTTG TACCCTGGAC CTGCTATAGC     1860

CGGTTGATTC TTCAATTGTA TTCCTAAAAG TTACTAAAAA AAAAAAAAAA AAAAAAAAA      1920

AAAACTCGAG                                                             1930

(2) INFORMATION FOR SEQ ID NO:2:

(i) SEQUENCE CHARACTERISTICS:
        (A) LENGTH: 480 amino acids
        (B) TYPE: amino acid
        (C) STRANDEDNESS:
        (D) TOPOLOGY: linear (xi) SEQUENCE DESCRIPTION: SEQ ID NO:2:

Met Val Lys Ile Cys Cys Ile Gly Ala Gly Tyr Val Gly Gly Pro Thr
1               5                   10                  15

Met Ala Val Ile Ala Leu Lys Cys Pro Asp Ile Glu Val Val Val
            20                  25                  30

Asp Ile Ser Lys Pro Arg Ile Glu Ala Trp Asn Ser Asp Thr Leu Pro
        35                  40                  45

Ile Tyr Glu Pro Gly Leu Asp Asp Val Val Lys Gln Cys Arg Gly Arg
    50                  55                  60

Asn Leu Phe Phe Ser Thr Asp Val Glu Lys His Val Ala Glu Ala Asp
65              70                  75                  80

Ile Ile Phe Val Ser Val Asn Thr Pro Thr Lys Thr Arg Gly Leu Gly
                85                  90                  95

Ala Gly Lys Ala Ala Asp Leu Thr Tyr Trp Glu Ser Ala Ala Arg Met
            100                 105                 110

Ile Ala Asp Val Ser Lys Ser Asp Lys Ile Val Glu Lys Ser Thr
        115                 120                 125

Val Pro Val Lys Thr Ala Glu Ala Ile Glu Lys Ile Leu Thr His Asn
    130                 135                 140
```

```
Ser Lys Gly Ile Asn Tyr Gln Ile Leu Ser Asn Pro Glu Phe Leu Ala
145                 150                 155                 160

Glu Gly Thr Ala Ile Glu Asp Leu Phe Lys Pro Asp Arg Val Leu Ile
                165                 170                 175

Gly Gly Arg Glu Thr Pro Glu Gly Arg Lys Ala Val Gln Ala Leu Lys
                180                 185                 190

Asp Val Tyr Ala His Trp Val Pro Glu Asp Arg Ile Leu Thr Thr Asn
            195                 200                 205

Leu Trp Ser Ala Glu Leu Ser Lys Leu Ala Ala Asn Ala Phe Leu Ala
        210                 215                 220

Gln Arg Ile Ser Ser Val Asn Ala Ile Ser Ala Leu Cys Glu Ala Thr
225                 230                 235                 240

Gly Ala Asn Val Thr Glu Val Ala Tyr Ala Val Gly Lys Asp Thr Arg
                245                 250                 255

Ile Gly Pro Lys Phe Leu Asn Ala Ile Val Gly Phe Gly Gly Ser Cys
                260                 265                 270

Phe Gln Lys Asp Ile Leu Asn Leu Val Tyr Ile Cys Glu Cys Asn Gly
                275                 280                 285

Leu Pro Glu Val Ala Asn Tyr Trp Lys Gln Val Ile Lys Ile Asn Asp
290                 295                 300

Tyr Gln Lys Ser Arg Phe Val Asn Arg Val Val Ser Ser Met Phe Asn
305                 310                 315                 320

Thr Val Ala Gly Lys Lys Ile Ala Val Leu Gly Phe Ala Phe Lys Lys
                325                 330                 335

Asp Thr Gly Asp Thr Arg Glu Thr Pro Ala Ile Asp Val Cys Lys Gly
                340                 345                 350

Leu Leu Gly Asp Lys Ala Gln Ile Ser Ile Tyr Asp Pro Gln Val Thr
                355                 360                 365

Glu Asp Gln Ile Gln Arg Asp Leu Ala Met Asn Lys Phe Asp Trp Asp
            370                 375                 380

His Pro Met His Leu Gln Pro Thr Ser Pro Thr Ala Val Lys Gln Val
385                 390                 395                 400

Ser Cys Val Trp Asp Ala Tyr Glu Ala Thr Lys Gly Ala His Gly Leu
                405                 410                 415

Cys Ile Leu Thr Glu Trp Asp Glu Phe Lys Thr Leu Asp Tyr Gln Lys
                420                 425                 430

Ile Phe Asp Asn Met Gln Lys Pro Ala Phe Val Phe Asp Gly Arg Asn
            435                 440                 445

Ile Val Asp Ser Glu Lys Leu Arg Glu Ile Gly Phe Ile Val Tyr Ser
        450                 455                 460

Ile Gly Lys Pro Leu Asp Ala Trp Leu Lys Asp Met Pro Ala Val Ala
465                 470                 475                 480

(2) INFORMATION FOR SEQ ID NO:3:

(i) SEQUENCE CHARACTERISTICS:
        (A) LENGTH: 1947 base pairs
        (B) TYPE: nucleic acid
        (C) STRANDEDNESS: single
        (D) TOPOLOGY: linear (xi) SEQUENCE DESCRIPTION: SEQ ID NO:3:

CACAACTCGT AGGCAGCGAG CGTCTCTCCT CTTCCTCTCC CACGCACCGC GCCAAGGAAG      60

GCAGAGAGAG ATCGCCGCTC CTCTTCTCTC CGTCGGTGGT GCGGTTGACC GCCCTCCTCG     120
```

```
AGCGAGATCT CGCTGCAGTC CCTCGAGATC TGGTCACAGA TCTATCCGAC AAGATGGTGA      180

AGATCTGCTG CATCGGTGCT GGCTATGTCG GTGGCCCAAC CATGGCTGTC ATTGCCCTAA      240

AGTGCCCAGA CATTGAGGTT GTCGTTGTTG ACATCTCCAA GCCCCGCATT GAGGCATGGA      300

ACAGCGACAC CCTCCCGATC TACGAGCCCG GCCTCGATGA TGTTGTGAAG CAGTGCAGGG      360

GCAGGAACCT CTTCTTCAGC ACTGATGTTG AGAAGCACGT CGCTGAGGCT GACATCATCT      420

TCGTCTCGGT GAACACCCCC ACCAAGACCC GTGGGCTTGG AGCTGGCAAG GCTGCCGACC      480

TCACCTACTG GGAGAGCGCT GCTCGTATGA TCGCCGATGT CTCCAAGTCT GACAAGATCG      540

TTGTCGAGAA GTCCACCGTC CCTGTCAAGA CCGCTGAGGC TATTGAGAAG ATCTTGACCC      600

ACAACAGCAA GGGCATCAAC TACCAGATCC TTTCCAACCC GGAGTTCCTT GCAGAGGGCA      660

CTGCTATTGA GGACCTGTTC AAGCCTGACA GAGTGCTCAT CGGTGGCCGG GAGACCCCCG      720

AGGGCAGGAA AGCCGTCCAG GTTCTCAAGG ATGTGTATGC TCACTGGGTT CCCGAGGACA      780

GGATCCTCAC CACCAACCTG TGGTCCGCTG AGCTCTCCAA GCTCGCCGCC AATGCGTTCT      840

TGGCACAGAG GATCTCCTCT GTCAATGCCA TCTCCGCTCT CTGCGAGGCA ACCGGAGCCA      900

ATGTCTCTGA GGTGGCTTAC GCCGTGGGCA AGGACACGAG AATTGGCCCC AAGTTCCTGA      960

ACGCCAGTGT TGGGTTCGGT GGCTCATGCT TCCAGAAGGA CATCCTGAAC CTGGTGTACA     1020

TCTGCGAGTG CAACGGCCTG CCCGAGGTGG CCAACTACTG GAAGCAGGTG ATCAGGATCA     1080

ACGACTACCA GAAGAGCCGG TTCGTGAACC GCGTCGTGGC CTCCATGTTC AACACCGTCG     1140

CCGGCAAGAA GATCGCCGTC CTCGGCTTCG CCTTCAAGAA AGACACCGGT GACACCAGGG     1200

AGACCCCGGC CATTGACGTC TGCAAGGGCC TGCTGGGCGA CAAGGCCCAG ATCAGCATCT     1260

ACGACCCCCA GGTGACGGAG GACCAGATCC AGCGGGACCT GGCCATGAAC AAGTTCGACT     1320

GGGACCACCC GATGCACCTG CAACCGACGA GCCCCACGGC CATTAAGCAG GTGAGCTGCG     1380

TGTGGGACGC GTACGAGGCC ACCAAGGGCG CCCACGGGGT GTGCATCCTG ACCGAGTGGG     1440

ACGAGTTCAA GACCCTGGAC TACCAGAAGA TCTTCGACAA CATGCAGAAG CCCGCCTTCG     1500

TCTTCGACGG CCGCAACATC GTCGACCCGG AGAAGCTGAG GGAGATCGGC TTCATCGTCT     1560

ACTCCATCGG CAAGCCGCTC GACGCCTGGC TTAAGGACAT GCCCGCGGTC GCTTAATTCG     1620

TCTGAGGTGC TCCATTGGAT TGGATCCGGG GAAGGAAGAG GAACTGGTTG ACCATTCTTC     1680

ATTACAGTTT GTTTTTTGCA GGATTCTTAA AAGTTGGACG GCGCTGCTAG TATTCCATGT     1740

TTCGTGTTTT CATATTGGAG GACGTCTGTA GATGTAAAAA ATCCTCGGGC GCTTGTGCTC     1800

GGCTTGAGGA AATATGCTTG TACGGTTGTA CCCTGGACCC GCTATAGCTG GTTGGTTCTT     1860

CAAGTTGTGT TCCTATAGAA GCCAAAGTTA CTACACGATC GATATGTTCT TTTTGCATAA     1920

TAACAATACT TGTCTCACGT TTCATCC                                         1947
```

(2) INFORMATION FOR SEQ ID NO:4:

(i) SEQUENCE CHARACTERISTICS:
        (A) LENGTH: 480 amino acids
        (B) TYPE: amino acid
        (C) STRANDEDNESS:
        (D) TOPOLOGY: linear (xi) SEQUENCE DESCRIPTION: SEQ ID NO:4:

```
Met Val Lys Ile Cys Cys Ile Gly Ala Gly Tyr Val Gly Gly Pro Thr
1               5                   10                  15

Met Ala Val Ile Ala Leu Lys Cys Pro Asp Ile Glu Val Val Val Val
            20                  25                  30
```

-continued

```
Asp Ile Ser Lys Pro Arg Ile Glu Ala Trp Asn Ser Asp Thr Leu Pro
         35                  40                  45

Ile Tyr Glu Pro Gly Leu Asp Asp Val Val Lys Gln Cys Arg Gly Arg
 50                  55                  60

Asn Leu Phe Phe Ser Thr Asp Val Glu Lys His Val Ala Glu Ala Asp
 65                  70                  75                  80

Ile Ile Phe Val Ser Val Asn Thr Pro Thr Lys Thr Arg Gly Leu Gly
                 85                  90                  95

Ala Gly Lys Ala Ala Asp Leu Thr Tyr Trp Glu Ser Ala Ala Arg Met
             100                 105                 110

Ile Ala Asp Val Ser Lys Ser Asp Lys Ile Val Val Glu Lys Ser Thr
             115                 120                 125

Val Pro Val Lys Thr Ala Glu Ala Ile Glu Lys Ile Leu Thr His Asn
 130                 135                 140

Ser Lys Gly Ile Asn Tyr Gln Ile Leu Ser Asn Pro Glu Phe Leu Ala
145                 150                 155                 160

Glu Gly Thr Ala Ile Glu Asp Leu Phe Lys Pro Asp Arg Val Leu Ile
                 165                 170                 175

Gly Gly Arg Glu Thr Pro Glu Gly Arg Lys Ala Val Gln Val Leu Lys
             180                 185                 190

Asp Val Tyr Ala His Trp Val Pro Glu Asp Arg Ile Leu Thr Thr Asn
             195                 200                 205

Leu Trp Ser Ala Glu Leu Ser Lys Leu Ala Ala Asn Ala Phe Leu Ala
210                 215                 220

Gln Arg Ile Ser Ser Val Asn Ala Ile Ser Ala Leu Cys Glu Ala Thr
225                 230                 235                 240

Gly Ala Asn Val Ser Glu Val Ala Tyr Ala Val Gly Lys Asp Thr Arg
                 245                 250                 255

Ile Gly Pro Lys Phe Leu Asn Ala Ser Val Gly Phe Gly Gly Ser Cys
             260                 265                 270

Phe Gln Lys Asp Ile Leu Asn Leu Val Tyr Ile Cys Glu Cys Asn Gly
             275                 280                 285

Leu Pro Glu Val Ala Asn Tyr Trp Lys Gln Val Ile Arg Ile Asn Asp
290                 295                 300

Tyr Gln Lys Ser Arg Phe Val Asn Arg Val Val Ala Ser Met Phe Asn
305                 310                 315                 320

Thr Val Ala Gly Lys Lys Ile Ala Val Leu Gly Phe Ala Phe Lys Lys
                 325                 330                 335

Asp Thr Gly Asp Thr Arg Glu Thr Pro Ala Ile Asp Val Cys Lys Gly
             340                 345                 350

Leu Leu Gly Asp Lys Ala Gln Ile Ser Ile Tyr Asp Pro Gln Val Thr
             355                 360                 365

Glu Asp Gln Ile Gln Arg Asp Leu Ala Met Asn Lys Phe Asp Trp Asp
370                 375                 380

His Pro Met His Leu Gln Pro Thr Ser Pro Thr Ala Ile Lys Gln Val
385                 390                 395                 400

Ser Cys Val Trp Asp Ala Tyr Glu Ala Thr Lys Gly Ala His Gly Val
                 405                 410                 415

Cys Ile Leu Thr Glu Trp Asp Glu Phe Lys Thr Leu Asp Tyr Gln Lys
             420                 425                 430

Ile Phe Asp Asn Met Gln Lys Pro Ala Phe Val Phe Asp Gly Arg Asn
             435                 440                 445

Ile Val Asp Pro Glu Lys Leu Arg Glu Ile Gly Phe Ile Val Tyr Ser
```

```
                  450                 455                 460
Ile Gly Lys Pro Leu Asp Ala Trp Leu Lys Asp Met Pro Ala Val Ala
465                 470                 475                 480

(2) INFORMATION FOR SEQ ID NO:5:

(i) SEQUENCE CHARACTERISTICS:
        (A) LENGTH: 237 base pairs
        (B) TYPE: nucleic acid
        (C) STRANDEDNESS: single
        (D) TOPOLOGY: linear (xi) SEQUENCE DESCRIPTION: SEQ ID NO:5:

ATGGCGGCGA CAATGGCAGT GACGACGATG GTGACCAGGA GCAAGGAGAG CTGGTCGTCA         60

TTGCAGGTCC CGGCGGTGGC ATTCCCTTGG AAGCCACGAG GTGGCAAGAC CGGCGGCCTC        120

GAGTTCCCTC GCCGGGCGAT GTTCGCCAGC GTCGGCCTCA ACGTGTGCCC GGGCGTCCCG        180

GCGGGGCGCG ACCCGCGGGA GCCCGATCCC AAGGTCGTCC GGGCGGCCGA CCTCATG          237
```

PLANT URIDINE DIPHOSPHATE-GLUCOSE DEHYDROGENASE GENES, PROTEINS, AND USES THEREOF

TECHNICAL FIELD

The present invention relates generally to methods of regulating the starch composition of plants. In particular, the present invention relates to novel UDP-glucose dehydrogenase (UDPGdH) genes, mutant and variant forms of the genes, and the use of such UDPGdH genes to produce plants with altered starch content due to modified UDPGdH activity.

BACKGROUND OF THE INVENTION

Polysaccharides produced by plants are useful for a variety of home and industrial applications. Plant gums and starches, for example, are used extensively in food and pharmaceutical industries, due to their emulsifying, stabilizing, thickening, and gel-forming properties (see, for example, Sandford and Baird, in *The Polysaccharides* (Aspinall, ed.), 2:411 (Academic Press 1983); Azczesniak, in *Gums and Stabilisers for the Food Industry* (Phillips et al., eds), 3:311 (Elsevier Applied Science Publishers 1986)). It would therefore be beneficial to alter plant polysaccharide synthesis to improve the quantities of polysaccharides or to provide new types of polysaccharides. Modifications of polysaccharide synthesis also can lead to improved plants. For example, increasing the amount of cell wall polysaccharide during development would improve resistance of developing seeds to pathogens and insects resulting in improved crop yields.

UDP-glucose is a nucleotide sugar that occupies a central position in plant metabolic pathways, including the synthesis of polysaccharides. UDP-glucose serves both as a precursor in sucrose synthesis and in the formation of those sugar nucleotides required for the synthesis of cell wall components. for example, UDP-glucose metabolism leads to amino sugars, cellulose, sucrose, fructans, and other non-cellulosic polysaccharides. In addition, UDP-glucose can substitute for ADP-glucose as a starch synthase substrate, at least in the waxy maize phenotype.

UDP-glucose dehydrogenase (UDPGdH) [EC 1.1.1.22] is an $NAD^+$-linked, four-electron transferring oxidoreductase that converts UDP-D-glucose (UDP-G) to UDP-D-glucuronic acid (UDP-GA) by two oxidation reactions in which UDP-6-aldehydo-D-glucose is an intermediate (Hempel et al., *Protein Science* 3:1074, 1994). UDP-GA is a precursor for sugar nucleotides, which are required for the biosynthesis of various components of hemicellulose, including arabinans, arabinogalactans, glucuronoarabinoxylans, rhamnogalacturonans, xylans, and xyloglucans. Evidence indicates that UDPGdH catalyzes the rate-limiting step in the synthesis of these cell wall precursors (Witt, *Journal of Plant Physiology* 140:276, 1992). UDPGdH is also centrally involved in the production of a variety of exopolysaccharide gums including xanthan gum and a variety of non-commercial gums produced by Streptococci (Ashtaputre and Shah, *Current Microbiology* 31:234, 1995); Lin et al., *Biochemical & Biophysical Research Communications* 207:223, 1995).

Since it is difficult to control the quantity and composition of hemicellulosic substances, there are problems with extraction of other useful plant-derived fibers and substances. Further, many naturally-occurring hemicellulosic substances and other polysaccharides derived from UDPGdH products are not useful commercial products due to their insufficient quantity and varying composition. Accordingly, there is a need for a means to improve and regulate the production of plant polysaccharides.

The present invention exploits novel genes that are highly and specifically expressed in developing plants to alter the regulation of UDPGdH activity, thus providing control of plant polysaccharide synthesis.

SUMMARY OF THE INVENTION

The present invention provides nucleic acid molecules that encode plant UDP-glucose dehydrogenase (UDPGdH), as well as modified UDPGdH proteins. More specifically, one aspect of the present invention provides isolated nucleic acid molecules encoding maize UDPGdH. Such nucleic acid molecules comprise a nucleotide sequence that encodes a polypeptide having the amino acid sequence of SEQ ID NO:2 or SEQ ID NO:4, or a variant thereof. Within one embodiment, the nucleotide sequence is either SEQ ID NO:1 or SEQ ID NO:3.

A second aspect of the present invention provides modified nucleic acid molecules encoding mutant forms of UDPGdH in which the catalytic cysteine 272 residue has been replaced with another amino acid residue. These mutant enzymes predominantly catalyze the conversion of UDP-D-glucose to UDP-6-aldehydo-D-glucose as the end product.

Also provided by the present invention are polypeptides encoded by such nucleotide sequences, vectors comprising such nucleotide sequences, and host cells that contain these vectors. Suitable vectors include expression vectors, such as a binary *Agrobacterium tumefaciens* plasmid vector. Suitable expression vectors can contain a seed-specific, tissue-specific, cell type-specific, or a plastid-specific promoter. Representative examples of suitable host cells include plant cells from maize, sorghum, wheat, rice, barley, oats, and potato. Preferred plant cells are maize cells.

Yet other aspects of the present invention include methods for producing a plant that expresses UDPGdH, comprising the steps of (a) introducing a vector as described above into an embryogenic plant cell, wherein the vector contains a UDPGdH gene in an expressible form, and (b) producing a plant from the embryogenic plant cell, wherein the plant expresses the UDPGdH gene. A nucleic acid molecule encoding UDPGdH also can be inserted in an expression vector to produce UDPGdH protein in host cells, such as bacterial, yeast, mammalian, insect or plant cells.

In one embodiment, over-expression of the UDPGdH gene in plant cells is used to increase polysaccharide synthesis. In other embodiments, expression in plant endosperm amyloplasts of UDPGdH enzyme activity is used to produce carboxylated starch. In additional embodiments, expression of exogenous UDPGdH enzyme activity by transgenic plants increases stem strength or stalk strength, and enhances resistance to insects and pathogens.

The present invention further provides methods for inhibiting endogenous UDPGdH activity in plant cells using UDPGdF nucleotide sequences. Plants comprising cells having diminished UDPGdH activity have enhanced value as an industrial source for starch and as animal feed. Such enzyme inhibition can be achieved, for example, by co-suppression. Alternatively, nucleotide sequences encoding at least a portion of the UDPGdH gene are inserted in the anti-sense direction into expression vectors to inhibit the expression of the UDPGdH gene in plant cells.

The present invention also provides methods of producing a plant that produces polysaccharides comprising 6-aldehydo-D-glucose moieties, and transgenic plants and plant cells that contain the nucleic acid molecules. or vectors, described herein. A method for producing polysaccharide that contains 6-aldehydo-D-glucose moieties, such as aldehydic starch, comprises the steps of (a) introducing into a plant cell an expression vector that comprises a mutant UDPGdH gene, and (b) growing the plant cell under conditions wherein the mutant UDPGdH gene is expressed. The present invention further includes polysaccharides comprising 6-aldehydo-D-glucose moieties, produced by transgenic plant cells.

The present invention also provides isolated nucleic acid molecules comprising a nucleotide sequence that encodes a polypeptide having UDP-glucose dehydrogenase (UDPGdH) activity, wherein the nucleic acid molecule is selected from the group consisting of (a) a polynucleotide that encodes an amino acid sequence having at least 80% identity to the amino acid sequence of either SEQ ID NO:2 or SEQ ID NO:4, with the proviso that the amino acid sequence is not encoded by the soybean UDPGdH gene having the nucleotide sequence of GenBank accession No. U53418, (b) a polynucleotide of at least 30 nucleotides in length which selectively hybridizes under stringent conditions to a nucleic acid molecule having the nucleotide sequence of either SEQ ID NO:1 or SEQ ID NO:3, (c) a polynucleotide that is complementary to polynucleotide (a) or (b), and (d) a polynucleotide comprising at least 30 contiguous nucleotides from polynucleotide (a), (b), or (c). A suitable polynucleotide (a) encodes a polypeptide that elicits the production of an antibody which is specifically reactive to a polypeptide having the amino acid sequence of SEQ ID NO:2 or SEQ ID NO:4. The present invention also contemplates expression cassettes that comprise a promoter operably linked to polynucleotides (a), (b), (c) or (d), in either the sense or anti-sense orientation. The present invention further provides recombinant host cells that comprise such expression cassettes. The present invention also includes isolated proteins comprising a polypeptide of at least ten contiguous amino acids encoded by such nucleic acid molecules.

The present invention also provides isolated nucleic acid molecules that encode a polypeptide having UDP-glucose dehydrogenase (UDPGdH) activity, and that can hybridize under stringent conditions with a nucleic acid molecule having either SEQ ID NO:1 or SEQ ID NO:3.

These and other aspects of the present invention will become evident upon reference to the following detailed description and attached drawings. In addition, various references are identified below and are incorporated by reference in their entirety.

BRIEF DESCRIPTION OF THE DRAWINGS

FIG. 1 presents the nucleotide sequence [SEQ ID NO:1] of the maize UDPGdH gene designated as "Zmudpgdh1."

FIG. 2 presents the amino acid sequence [SEQ ID NO:2] encoded by the maize UDPGdH Zmudpgdh1 gene.

FIG. 3 presents the nucleotide sequence [SEQ ID NO:3] of the maize UDPGdH gene designated as "Zmudpgdh2."

FIG. 4 presents the amino acid sequence [SEQ ID NO:4] encoded by the maize UDPGdH Zmudpgdh2 gene.

DETAILED DESCRIPTION OF THE INVENTION

1. Definitions

In the description that follows, a number of terms are used extensively. The following definitions are provided to facilitate understanding of the invention.

A "structural gene" is a nucleotide sequence that is transcribed into messenger RNA (mRNA), which is then translated into a sequence of amino acids characteristic of a specific polypeptide.

As used herein, "nucleic acid" or "nucleic acid molecule" refers to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally-occurring nucleotides (such as deoxyribonucleotides and ribonucleotides), or analogs of naturally-occurring nucleotides (e.g., α-enantiomeric forms of naturally-occurring nucleotides), or a combination of both. Modified nucleotides can have modifications in sugar moieties and/or in pyrimidine or purine base moieties. Sugar modifications include, for example, replacement of one or more hydroxyl groups with halogens, allkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocylcic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids," which comprise naturally-occurring or modified nucleic acid bases attached to a polyamide backbone. Nucleic acids can be either single stranded or double stranded.

An "isolated nucleic acid molecule" is a nucleic acid molecule that is not integrated in the genomic DNA of an organism. For example, an isolated DNA molecule that encodes maize UDPGdH is a DNA fragment that has been separated from the genomic DNA of maize. Another example of an isolated nucleic acid molecule is a chemically-synthesizednucleic acid molecule that is not integrated in the genome of an organism.

As used herein, a "uridine diphosphate glucose dehydrogenase gene" (UDPGdH gene) is a nucleic acid molecule that encodes a protein having oxidoreductase activity. Specifically, a UDPGdH enzyme catalyzes a two-step reaction in which UDP-D-glucose is converted to UDP-6-aldehydo-D-glucose, which, in turn, is converted to UDP-D-glucuronic acid. The amino acid sequence of representative forms of maize UDPGdH have been deduced and are presented in SEQ ID NOs:2 and 4.

Within the context of this invention, a "UDPGdH variant gene" refers to a nucleic acid molecule that encodes a polypeptide having an amino acid sequence that is a modification of SEQ ID NO:2 or SEQ ID NO:4. Such variants include naturally-occurring polymorphisms of maize UDPGdH genes (e.g., the Zmudpgdh1 and Zmudpgdh2 genes are such variants), as well as synthetic genes that contain conservative amino acid substitutions of the amino acid sequence of SEQ ID NOs:2 and 4. Additional forms of UDPGdH gene variants are nucleic acid molecules that contain insertions or deletions of the maize UDPGdH-encoding sequences, described herein.

UDPGdH variants should preferably have at least an 80% amino acid sequence identity to SEQ ID NO:2 or SEQ ID NO:4, and within certain embodiments, greater than 85%, 90%, 91%, 92%, 94%, 96%, or 98% identity. As an example, the amino acid sequences of Zmudpgdh1 and Zmudpgdh2 share greater than 98% identity, and therefore, each can be considered as a variant of the other On the other hand, the amino acid sequence of the soybean UDPGdH gene (GenBank accession No. U53418) described by Tenhaken and Thulke, *Plant Physiol.* 112:1127 (1996), shares only a 90.8% or a 90.2% identity with SEQ ID NO:2 or SEQ ID NO:4, respectively. Accordingly, this soybean UDPGdH gene is not a UDPGdH variant having greater than 91% identity to the Zmudpgdh1 and Zmudpgdh2 genes. The present invention contemplates UDPGdH variants having at least an 80% amino acid sequence identity to SEQ ID NO:2 or SEQ ID NO:4, with the proviso that such variants do not include the soybean UDPGdH polypeptide encoded by the nucleotide sequence designated as GenBank accession No. U53418.

Alternatively, UDPGdH variants can be identified by having at least a 70% nucleotide sequence identity to SEQ ID NO:1 or SEQ ID NO:3, with the proviso that such variants do not include the soybean UDPGdH gene having the nucleotide sequence designated as GenBank accession No. U53418. Moreover, the present invention contemplates UDPGdH variants having greater than 73%, 76%, 80%, 85%, 90%, or 95% identity to SEQ ID NO:1 or SEQ ID NO:3. Again, the nucleotide sequences of Zmudpgdh1 and Zmudpgdh2 share greater than 91% identity, and therefore, each can be considered as a variant of the other. In contrast, the soybean UDPGdH gene of Tenhaken and Thulke, supra, shares only a 71.4% or a 72.1% identity with SEQ ID NO:1 and SEQ ID NO:3, respectively. Accordingly, this soybean UDPGdH gene is not a UDPGdH variant having greater than 73% identity to the Zmudpgdh1 and Zmudpgdh2 genes.

Regardless of the particular nucleotide sequence of a variant UDPGdH gene, the gene encodes an enzyme that catalyzes the typical two-step reaction described above. More specifically, variant UDPGdH genes encode enzymes which exhibit at least 50%, and preferably, greater than 70, 80 or 90%, of the activity of the enzyme having the amino acid sequence of SEQ ID NO:2 or SEQ ID NO:4, as determined by the assay described herein.

The present invention includes functional fragments of UDPGdH genes. Within the context of this invention, a "functional fragment" of a UDPGdH gene refers to a nucleic acid molecule that encodes a portion of a UDPGdH polypeptide which possesses UDPGdH enzymatic activity. For example, a functional fragment of a maize UDPGdH gene described herein comprises a portion of the nucleotide sequence of SEQ ID NO:1 or SEQ ID NO:3, and encodes a polypeptide that can convert UDP-D-glucose to UDP-D-glucuronic acid. Similarly, a "functional fragment" of a UDPGdH enzyme is a polypeptide exhibiting UDPGdH activity.

A "mutant UDPGdH gene" is a nucleic acid molecule that encodes an enzyme that catalyzes only the first step of the UDPGdH enzyme reaction. That is, the product of a mutant UDPGdH enzyme is predominantly UDP-6-aldehydo-D-glucose, not UDP-D-glucuronic acid. More specifically, a mutant UDPGdH enzyme produces more than 70%, and preferably, more than 80 or 90%, UDP-6-aldehydo-D-glucose as the end product. Structurally, a mutant UDPGdH gene is characterized by the substitution of a cysteine residue at position 272 of SEQ ID NO:2 or SEQ ID NO:4 with another amino acid residue. Suitable substitute amino acid residues include alanine, serine, threonine, methionine, or glycine residues.

A "functional fragment of a UDPGdH mutant gene" refers to a nucleic acid molecule that encodes a portion of a mutant UDPGdH polypeptide which possesses mutant UDPGdH enzymatic activity. One example of a functional fragment of a mutant UDPGdH gene is a nucleic acid molecule (1) that encodes a portion of the amino acid sequence of SEQ ID NO:2 or SEQ ID NO:4, including the amino acid at position 272 which is not a cysteine residue, and (2) that encodes a polypeptide that converts UDP-D-glucose to UDP-6-aldehydo-D-glucose, rather than UDP-D-glucuronic acid, as a predominant final product.

The terms "stringent conditions" or "stringent hybridization conditions" refer to conditions under which a test nucleic acid molecule will hybridize to a target reference nucleotide sequence, to a detectably greater degree than other sequences (e.g., at least two-fold over background). Stringent conditions are sequence-dependent and will differ in experimental contexts. For example, longer sequences hybridize specifically at higher temperatures. Generally, stringent conditions are selected to be about 5° C. to about 20° C. lower, and preferably, 5° C. lower, than the thermal melting point (Tm) for the specific target sequence at a defined ionic strength and pH. The Tm is the temperature (under defined ionic strength and pH) at which 50% of a complementary target sequence hybridizes to a perfectly matched probe. Typically, stringent conditions will be those in which the salt concentration is less than about 1.0 M Na ion concentration (or other salts), typically about 0.01 to 1.0 M Na ion concentration (or other salts), at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30°)% formamide, 1 M NaCl, 1% SDS at 37° C., and a wash in 2×SSC at 50° C. Exemplary high stringency conditions include hybridization in 50% formamide, 1 M NaCl, 1% SDS at 37° C., and a wash in 0.1×SSC at 60° C.

An "isolated polypeptide" is a polypeptide that is essentially free from contaminating cellular components, such as carbohydrate, lipid, or other proteinaceous impurities associated with the polypeptide in nature. That a particular protein preparation contains an isolated polypeptide can be shown by the appearance of a single band following sodium dodecyl sulfate (SDS)-polyacrylamide gel electrophoresis of the protein preparation and Coomassie Brilliant Blue staining of the gel.

A "promoter" is a nucleotide sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

A "core promoter" contains essential nucleotide sequences for promoter function, including the TATA box and start of transcription. By this definition, a core promoter may or may not have detectable activity in the absence of specific sequences that may enhance the activity or confer tissue specific activity. For example, the Cauliflower Mosaic Virus (CaMV) 35S core promoter consists of about 33 nucleotides 5'-ward of the transcriptional start site of the 35S genome.

A "regulatory element" is a nucleotide sequence that modulates the activity of a promoter. For example, a regulatory element may contain a nucleotide sequence that binds with cellular factors enabling transcription exclusively or preferentially in particular cells, tissues, organelles, or plastids. These types of regulatory elements are normally associated with genes that are expressed in a "cell-specific," "tissue-specific," "organelle-specific," or "plastid-specific" manner.

An "enhancer" is a type of regulatory element that can increase the efficiency of transcription, regardless of the distance or orientation of the enhancer relative to the start site of transcription.

A "transit peptide" refers to an amino acid sequence that directs the transport of a fused protein into a plant organelle or plastid. Such organelles and plastids include but are not limited to leucoplasts, amyloplasts, chloroplasts, or mitochondria.

A "fusion protein" is a hybrid protein expressed by a nucleic acid molecule comprising nucleotide sequences of at least two genes. In the context of the present invention, a fusion protein comprises UDPGdH amino acid sequences (or mutant UDPGdH amino acid sequences) and additional amino acid sequences. For example, a fusion protein can comprise amino acid sequences of a transit peptide joined with an amino acid sequence of at least part of a UDPGdH enzyme. As another example, a fusion protein can comprise at least part of a UDPGdH sequence fused with a polypeptide that binds an affinity matrix. Such fusion proteins are useful for isolating large quantities of UDPGdH protein with affinity chromatography.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term "expression" refers to the biosynthesis of a gene product. For example, in the case of a structural gene, expression involves transcription of the structural gene into mRNA and the translation of mRNA into one or more polypeptides. In contrast, the expression of a ribozyme gene, discussed below, results in the biosynthesis of a nucleic acid as the end product.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites at which foreign nucleotide sequences can be inserted in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, gene expression is placed under the control of a promoter, and optionally, under the control of at least one regulatory element. Such a gene is said to be "operably linked to" the promoter. Similarly, a regulatory element and a promoter are operably linked if the regulatory element modulates the activity of the promoter. The product of a gene expressed by an expression vector is referred to as an "exogenous" gene product. For example, a maize cell comprising a vector that expresses a maize UDPGdH gene will contain mRNA of exogenous UDPGdH encoded by vector nucleotide sequences (i.e., this UDPGdH mRNA is encoded by an exogenous gene). Such a plant cell may also contain "endogenous" UDPGdH mRNA that is a transcript of genomic UDPGdH nucleotide sequences.

A "recombinant host" may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

A "transgenic plant" is a plant having one or more plant cells that contain an expression vector.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

Similarly, an "anti-sense oligonucleotide specific for UDPGdH" or a "UDPGdH anti-sense oligonucleotide" is an oligonucleotide having a sequence (a) capable of forming a stable triplex with a portion of the UDPGdH gene, or (b) capable of forming a stable duplex with a portion of an mRNA transcript of the UDPGdH gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

2. Isolation of UDPGdH Genes

As described herein, DNA molecules encoding a maize UDPGdH gene have been isolated from a cDNA library. See Example 1. The nucleotide and predicted amino acid sequences of two maize UDPGdH genes are shown in FIGS. 1–4. DNA molecules encoding these maize UDPGdH genes can be obtained by screening a maize cDNA or genomic library using polynucleotide probes based upon SEQ ID NO:1 or SEQ ID NO:3. These techniques are standard and well-established.

For example, the first step in the preparation of a cDNA library is to isolate RNA from plant cells. Total RNA can be prepared from maize tissue using techniques well-known to those in the art. In general, RNA isolation techniques must provide a method for breaking plant cells, a means of inhibiting RNase-directed degradation of RNA, and a method of separating RNA from DNA, protein, and polysaccharide contaminants. For example, total RNA can be isolated by freezing plant tissue in liquid nitrogen, grinding the frozen tissue with a mortar and pestle to lyse the cells, extracting the ground tissue with a solution of phenol/chloroform to remove proteins, and separating RNA from the remaining impurities by selective precipitation with lithium chloride (see, for example, Ausubel et al. (eds.), *Current Protocols in Molecular Biology*, pages 4.3.1–4.3.4 (Wiley Interscience 1990) ["Ausubel (1990)"]; Sharrock et al., *Genes and Development* 3: 1745, 1989).

Alternatively, total RNA can be isolated from plant tissue by extracting ground tissue with guanidinium isothiocyanate, extracting with organic solvents, and separating RNA from contaminants using differential centrifugation (see, for example, Strommer et al., "Isolation and characterization of Plant mRNA," in *Methods in Plant Molecular Biology and Biotechnology*, Glick et al. (eds.), pages 49–65 (CRC Press 1993)).

In order to construct a cDNA library, poly(A)$^+$ RNA must be isolated from a total RNA preparation. Poly(A)$^+$ RNA can be isolated from total RNA by using the standard technique of oligo(dT)-cellulose chromatography (see, for example, Strommer et al., supra.).

Double-stranded cDNA molecules are synthesized from poly(A)+ RNA using techniques well-known to those in the art. (see, for example, Ausubel (1990) at pages 5.5.2–5.6.8). Moreover, commercially available kits can be used to synthesize double-stranded cDNA molecules. For example, such kits are available from Life Technologies (Gaithersburg, Md.), Clontech Laboratories, Inc. (Palo Alto, Calif.), Promega Corporation (Madison, Wis.) and Stratagene Cloning Systems (La Jolla, Calif.).

Various cloning vectors are appropriate for the construction of a maize cDNA library. For example, a cDNA library can be prepared in a vector derived from bacteriophage, such as a λgt10 vector (see, for example, Huynh et al., "Constructing and Screening cDNA Libraries in λgt10 and λgt11," in DNA Cloning: A Practical Approach Vol. I, Glover (ed.), page 49 (IRL Press, 1985)).

Alternatively, double-stranded cDNA molecules can be inserted into a plasmid vector, such as a pBluescript vector (Stratagene Cloning Systems; La Jolla, Calif.), a LambdaGEM-4 (Promega Corp.) or other commercially available vectors. Suitable cloning vectors also can be obtained from the American Type Culture Collection (Rockville, Md.).

In order to amplify the cloned cDNA molecules, the cDNA library is inserted into a prokaryotic host, using standard techniques. For example, a cDNA library can be introduced into competent *E. coli* DH5 cells, which can be obtained from Life Technologies, Inc. (Gaithersburg, Md.).

A plant genomic DNA library can be prepared by means well-known in the art (see, for example, Slightom et al. "Construction of λ Clone Banks," in *Methods in Plant Molecular Biology and Biotechnology*, Glick et al. (eds.), page 121 (CRC Press 1993)). Genomic DNA can be isolated by lysing plant tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient (see, for example, Ausubel (1990) at pages 2.3.1–2.3.3).

DNA fragments that are suitable for the production of a genomic library can be obtained by the random shearing of genomic DNA or by the partial digestion of genomic DNA with restriction endonucleases (see, for example, Ausubel (1990) at pages 5.3.2–5.4.4, and Slightom et al., supra). Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are disclosed by Slightom et al., supra, and are well-known in the art (also see Ausubel (1990) at pages 3.0.5–3.17.5).

Alternatively, a plant genomic library can be obtained from a commercial source such as Clontech Laboratories, Inc., (Palo Alto, Calif.) or Stratagene Cloning Systems (La Jolla, Calif.).

A library containing cDNA or genomic clones can be screened with one or more polynucleotide probes based upon SEQ ID NO:1 or SEQ ID NO:3 (see, for example, Ausubel (1990) at pages 6.0.3–6.6.1; Slightom et al., supra; Raleigh et al., *Genetics* 122:279, 1989).

As an alternative, a UDPGdH gene can be obtained by synthesizing DNA molecules using mutually priming long oligonucleotides and UDPGdH sequences described herein (see, for example, Ausubel (1990) at pages 8.2.8 to 8.2.13 (1990); Wosnick et al., *Gene* 60:115, 1987; and Ausubel et al. (eds.), *Short Protocols in Molecular Biology*, 3rd Edition, pages 8-8 to 8-9 (John Wiley & Sons, Inc. 1995) ["Ausubel (1995)"]). Established techniques using the polymerase chain reaction provide the ability to synthesize DNA molecules at least two kilobases in length (Adang et al., *Plant Molec. Biol.* 21:1131, 1993); Bambot et al., *PCR Methods and Applications* 2:266, 1993); Dillon et al., "Use of the Polymerase Chain Reaction for the Rapid Construction of Synthetic Genes," in *Methods in Molecular Biology, Vol. 15: PCR Protocols: Current Methods and Applications*, White (ed.), pages 263–268, (Humana Press, Inc. 1993); Holowachuk et al., *PCR Methods Appl.* 4:299, 1995).

3. Preparation of Variant and Mutant UDPGdH Genes

Additional nucleic acid molecules encoding UDPGdH genes can also be obtained by screening various cDNA or genomic libraries with polynucleotide probes having nucleotide sequences based upon SEQ ID NO:1 or SEQ ID NO:3. Suitable libraries can be prepared by obtaining nucleic acids from tissue of any plant and constructing a library according to standard methods (see, for example, Ausubel (1995) at pages 2-1 to 2-13 and 5-1 to 5-6). Monocotyledonous plant species are preferred sources of nucleic acids. For example, nucleic acids can be obtained from tissues of wheat, barley, rice, sorghum, or oats to construct libraries suitable for obtaining additional UDPGdH-encoding sequences.

Nucleic acid molecules that encode UDPGdH can also be obtained using the polymerase chain reaction (PCR) with oligonucleotide primers having nucleotide sequences that are based upon the nucleotide sequences of maize UDPGdH genes, as described herein. General methods for screening libraries with PCR are provided by, for example, Yu et al., "Use of the Polymerase Chain Reaction to Screen Phage Libraries," in *Methods in Molecular Biology, Vol. 15: PCR Protocols: Current Methods and Applications*, White (ed.), pages 211–215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology, Vol. 15: PCR Protocols: Current Methods and Applications*, White (ed.), pages 317–337 (Humana Press, Inc. 1993).

Anti-UDPGdH antibodies, produced as described below, can also be used to isolate DNA sequences that encode enzymes from cDNA libraries constructed from mRNA from various species. For example, the antibodies can be used to screen λgt11 expression libraries, or the antibodies can be used for immunoscreening, following hybrid selection and translation (see, for example, Ausubel (1995) at pages 6–12 to 6–16; and Margolis et al., "Screening λ expression libraries with antibody and protein probes," in DNA Cloning 2: Expression Systems, 2nd Edition, Glover et al. (eds.), pages 1–14 (Oxford University Press 1995)). As an illustration, Tenhaken and Thulke, *Plant Physiol.* 112:1127 (1996), used antibody screening to isolate soybean UDPGdH cDNA molecules from an expression library.

UDPGdH gene variants can also be constructed synthetically. For example, a nucleic acid molecule can be devised that encodes, a polypeptide having a conservative amino acid change, compared with the amino acid sequence of SEQ ID NO:2 or SEQ ID NO:4. That is, variants can be obtained that contain one or more amino acid substitutions of SEQ ID NOs:2 or 4, in which an alkyl amino acid is substituted for an alkyl amino acid in a maize UDPGdH amino acid sequence, an aromatic amino acid is substituted for an aromatic amino acid in the maize UDPGdH amino acid sequence, a sulfur-containing amino acid is substituted for a sulfur-containing acid in the maize UDPGdH amino acid sequence, a hydroxy-amino containing amino acid is substituted for a hydroxy-containing amino acid in the maize UDPGdH amino acid sequence, an acidic amino acid is substituted for an acidic amino acid in the maize UDPGdH amino acid sequence, a basic amino acid is substituted for a basic amino acid in the maize UDPGdH amino acid sequence, or a dibasic monocarboxylic amino acid is substituted for a dibasic monocarboxylic amino acid in the maize UDPGdH amino acid sequence.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

Conservative amino acid changes in the maize UDPGdH gene can be introduced by substituting nucleotides for the nucleotides recited in SEQ ID NO:1 or SEQ ID NO:3. Such "conservative amino acid" variants can be obtained, for example, by oligonucleotide-directed mutagenesis, linker-scanning mutagenesis, mutagenesis using the polymerase chain reaction, and the like (see Ausubel (1990) at pages 8.0.3–8.5.9; Ausubel (1995) at pages 8-10 to 8-22; and Mcpherson (ed.), *Directed Mutagenesis: A Practical Approach* (IRL Press 1991)). The ability of such variants to convert UDP-D-glucose to UDP-D-glucuronic acid can be determined using a standard enzyme activity assay, such as the assay described herein.

Accordingly, a UDPGdH variant gene can be identified by function on the basis that a variant gene can express a UDPGdH enzyme that catalyzes a reaction in which UDP-D-glucose is converted to UDP-D-glucuronic acid. A variant UDPGdH gene can be identified on the basis of structure by determining the level of similarity between the nucleotide sequence of the variant with the nucleotide sequences of SEQ ID NOs:1 or 3, as detailed above.

An alternative approach to identifying a UDPGdH variant gene on the basis of structure is to determine whether a nucleic acid molecule encoding a potential variant UDPGdH gene can hybridize under stringent conditions to a nucleic acid molecule having the nucleotide sequence of SEQ ID NOs:1 or 3. As discussed above, stringent conditions are selected to be about 5° C. to about 20° C. lower than the thermal melting point for a reference UDPGdH gene sequence at a defined ionic strength and pH. Typically, stringent wash conditions following hybridization are those in which the salt concentration is about 0.02 molar at pH 7 and the temperature is at least about 50, 55, or 60° C. Nucleic acid hybridization methods are well-known to those of skill in the art (see, for example, Hames and Higgins, *Nucleic Acid Hybridisation: A Practical Approach* (IRL Press, 1985); Tijssen, *Laboratory Techniques in Biochemistry and Molecular Biology—Hybridization with Nucleic Acid Probes, Part I*, Chapter 2 "Overview of principles of hybridization and the strategy of nucleic acid probe assays" (Elsevier 1993), Ausubel (1995) at pages 2-36 to 2-40).

Preferably, a nucleic acid molecule having variant UDPGdH sequences can bind with a nucleic acid molecule having a sequence from SEQ ID NO:1 or 3 under conditions of high stringency.

A test nucleic acid molecule that does not hybridize to a reference nucleic acid molecule having the nucleotide sequence of SEQ ID NOs. 1 or 3 under stringent conditions may still represent a variant UDPGdH gene if the polypeptide encoded by the potential UDPGdH variant gene has an amino acid sequence that is substantially identical to either SEQ ID NOs. 2 or 4. This is so because the nucleotide sequence of a particular UDPGdH variant gene may represent the maximum codon degeneracy permitted by the genetic code. One indication that two nucleic acid sequences encode substantially identical polypeptides is that the polypeptide encoded by a first nucleic acid sequence is immunologically cross-reactive with the polypeptide encoded by the second nucleic acid sequence.

With regard to substantially identical amino acid sequences, UDPGdH variants should preferably have at least an 80% amino acid sequence identity to SEQ ID NO:2 or SEQ ID NO:4, and within certain embodiments, greater than 85%, 90%, 91%, 92%, 94%, 96%, or 98% identity over a specified comparison window. Preferably, optimal alignment is conducted using the homology alignment algorithm of Needleman and Wunsch, *J. Mol. Biol.* 48:443, 1970.

Routine deletion analyses of nucleic acid molecules can be performed to obtain "functional fragments" of a nucleic acid molecule that encodes UDPGdH. As an illustration, DNA molecules having the nucleotide sequence of SEQ ID NO:1 or SEQ ID NO:3 can be digested with Bal31 nuclease to obtain a series of nested deletions. The fragments are then inserted into expression vectors in proper reading frame, and the expressed polypeptides are isolated and tested for UDPGdH enzyme activity. One alternative to exonuclease digestion is to use oligonucleotide-directed mutagenesis to introduce deletions or stop codons to specify production of a desired fragment. Alternatively, particular fragments of a maize UDPGdH gene can be synthesized using the polymerase chain reaction. Standard techniques for functional analysis of proteins are described by, for example, Treuter et al., *Molec. Gen. Genet.* 240:113 (1993); Content et al., "Expression and preliminary deletion analysis of the 42 kDa 2–5A synthetase induced by human interferon," in *Biological Interferon Systems, Proceedings of ISIR-TNO Meeting on Interferon Systems*, Cantell (ed.), pages 65–72 (Nijhoff 1987); Herschman, "The EGF Receptor," in *Control of Animal Cell Proliferation, Vol.* 1, Boynton et al., (eds.) pages 169–199 (Academic Press 1985); Coumailleau et al.,*J. Biol. Chem.* 270:29270 (1995); Fukunaga et al., *J. Biol. Chem.* 270:25291 (1995); Yamaguchi et al., *Biochem. Pharmacol.* 50:1295 (1995); and Meisel et al., *Plant Molec. Biol.* 30:1 (1996).

The present invention also contemplates functional fragments of a UDPGdH gene that have conservative amino acid changes.

Furthermore, deletions and/or insertions of the UDPGdH gene can be constructed by any of a variety of known methods. For example, the gene can be digested with restriction enzymes and religated such that the resultant sequence lacks a sequence of the native gene, or religated with an additional DNA fragment such that the resultant sequence contains an insertion or large substitution. Other standard methods for generating variant sequences may be used as described, for example, by Sambrook and Ausubel (1995). Verification of variant sequences is typically accomplished by restriction enzyme mapping, sequence analysis, or probe hybridization.

A mutant UDPGdH gene of the present invention is a nucleic acid molecule encoding an enzyme that catalyzes predominantly the conversion of UDP-D-glucose to UDP-6-aldehydo-D-glucose, rather than UDP-D-glucuronic acid. Such mutants are obtained by replacing the cysteine residue at position 272 of SEQ ID NOs:2 or 4 with another amino acid residue. Examples of suitable substitute amino acid residues include alanine, methionine, serine, glycine, and threonine residues. Preferred substitute amino residues include alanine, serine, and threonine residues. Mutagenesis techniques are well-known to those of skill in the art, as discussed above.

4. Expression of Cloned UDPGdH Genes

To express the polypeptide encoded by a GFAT gene, a nucleotide sequence encoding the enzyme must be operably linked to nucleotide sequences that control transcriptional expression in an expression vector and then, introduced into either a prokaryotic or eukaryotic host cell. In addition to nucleotide sequences that control transcription, such as promoters and regulatory elements, expression vectors can include translational regulatory sequences, and a marker gene which is suitable for selection of cells that carry the expression vector.

Depending on the desired use of an expressed UDPGdH polypeptide, it may be advantageous to produce UDPGdH polypeptide as a fusion protein. For example, a fusion protein can be expressed that comprises both UDPGdH sequences and a portion that binds with an affinity matrix. In this way, large quantities of UDPGdH polypeptides can be obtained by cleaving the polypeptides from fusion protein bound to an affinity chromatography column. Alternatively, it may be desirable to express a fusion protein comprising a UDPGdH sequence and a transit peptide for targeting the enzyme to a particular organelle. Such transit peptides are discussed below. Accordingly, the present invention contemplates fusion proteins comprising UDPGdH polypeptides.

Suitable promoters for expression of UDPGdH polypeptides in a prokaryotic host can be repressible, constitutive, or inducible. Suitable promoters are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of Bacillus, Streptomyces promoters, the int promoter of bacteriophage lambda, the bla promoter of pBR322, and the CAT promoter of the chloramphenicol acetyl transferase gene. Prokaryotic promoters are reviewed by Glick, *J. Ind. Microbial.* 1:277 (1987); Watson et al., *Molecular Biology of the Gene*, 4th Ed. (Benjamin Cummins 1987); Ausubel et al. (1990, 1995), and Sambrook et al., supra.

Preferred prokaryotic hosts include *E. coli* and *Bacillus subtilus*. Suitable strains of *E. coli* include BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (Ed.), *Molecular Biology Labfax*, Academic Press (1991)). Suitable strains of *Bacillus subtilis* include BR151, YB886, MI119, MI120, and B170 (see, for example, Hardy, "Bacillus Cloning Methods," in *DNA Cloning: A Practical Approach*, Glover (Ed.), (IRL Press 1985)).

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems*, 2nd Edition, Glover et al. (eds.), page 15 (Oxford University Press 1995); Ward et al., "Genetic Manipulation and Expression of Antibodies," in *Monoclonal Antibodies: Principles and Applications*, page 137 (Wiley-Liss, Inc. 1995); and Georgiou, "Expression of Proteins in Bacteria," in *Protein Engineering: Principles and Practice*, Cleland et al. (eds.), page 101 (John Wiley & Sons, Inc. 1996)).

Expression vectors also can be introduced into eukaryotic hosts, such as mammalian cells, yeast cells, insect cells, and plant cells. Expression vectors that are suitable for production of UDPGdH protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence.

Examples of mammalian host cells include human embryonic kidney cells (293-HEK; ATCC CRL 1573), baby hamster kidney cells (BHK-21; ATCC CRL 8544), canine kidney cells (MDCK; ATCC CCL, 34), Chinese hamster ovary cells (CHO-K1; ATCC CCL61), rat pituitary cells ($GH_1$; ATCC CCL82), HeLa S3 cells (ATCC CCL2.2), rat hepatoma cells (H-4-II-E; ATCC CRL, 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Nucleotide sequences that control transcription include a promoter sufficient to direct the initiation of RNA synthesis. Suitable eukaryotic promoters include the promoter of the mouse metallothionein I gene [Hamer et al., *J. Molec. Appl. Genet.* 1:273, 1982)], the TK promoter of Herpes virus [McKnight, *Cell* 31:355, 1982)], the SV40 early promoter [Benoist et al., *Nature* 290:304, 1981)], the Rous sarcoma virus promoter [Gorman et al., *Proc. Nat'l Acad. Sci. USA* 79:6777, 1982), the cytomegalovirus promoter [Foecking et al., *Gene* 45:101, 1980)], and the mouse mammary tumor virus promoter. See, generally, Etcheverry, "Expression of Engineered Proteins in Mammalian Cell Culture," in *Protein Engineering: Principles and Practice*, Cleland et al. (eds.), pages 163–181 (John Wiley & Sons, Inc. 1996).

Alternatively, a prokaryotic promoter, such as the bacteriophage T3 RNA polymerase promoter, can be used to control fusion gene expression if the prokaryotic promoter is regulated by a eukaryotic promoter (see, for example, Zhou et al., *Mol. Cell. Biol.* 10:4529, 1990; Kaufman et al., *Nucl. Acids Res.* 19:4485, 1991).

The baculovirus system provides an efficient means to introduce cloned UDPGdH genes into insect cells. Suitable expression vectors are based upon the *Autographa californica* multiple nuclear polyhedrosis virus (AcMNPV), and contain well-known promoters such as Drosophila heat shock protein (hsp) 70 promoter, *Autographa californica* nuclear polyhedrosis virus immediate-early gene promoter (ie-1) and the delayed early 39K promoter, baculovirus p10 promoter, and the Drosophila metallothionein promoter. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as Drosophila Schneider-2 cells. Established techniques for producing recombinant proteins in baculovirus systems are provided by Bailey et al., "Manipulation of Baculovirus Vectors," in *Methods in Molecular Biology, Volume 7: Gene Transfer and Expression Protocols*, Murray (ed.), pages 147–168 (The Humana Press, Inc. 1991), by Patel et al., "The baculovirus expression system," in *DNA Cloning 2: Expression Systems*, 2nd Edition, Glover et al. (eds.), pages 205–244 (Oxford University Press 1995), by Ausubel (1995) at pages 16-37 to 16-57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183–218 (John Wiley & Sons, Inc. 1996).

Promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. One skilled in the art will appreciate that there are a wide variety of suitable vectors for expression in yeast cells.

A UDPGdH expression vector can also include a nucleotide sequence encoding a secretion signal. In this way, recombinant UDPGdH protein can be recovered from the periplasmic space of host cells or from fermentation medium. Secretion signals suitable for use are widely available and are well-known in the art (see, for example, von Heijne, *J. Mol. Biol.* 184:99, 1985). Prokaryotic and eukaryotic secretion signals that are functional in *E. coli* (or other host cells) may be employed. Suitable secretion signals include, but are not limited to, those encoded by the following *E. coli* genes: pelB, phoA, ompA, ompT, ompF, ompC, beta-lactamase, and alkaline phosphatase (see, for example, Lei et al., *J. Bacteriol.* 169:4379, 1987). As a further example, the signal sequence from the cek2 gene is useful for secretion in recombinant insect cells. Those of skill in the art are aware of secretion signals that are functional in prokaryotic, yeast, insect or mammalian cells to secrete proteins from those cells.

An expression vector can be introduced into bacterial, mammalian, insect, and yeast host cells using a variety of techniques including calcium chloride transformation, liposome-mediated transfection, electroporation, and the like (see, for example, Ausubel (1995) at pages 1-1 to 1-24). Preferably, transfected cells are selected and propagated wherein the expression vector is stably integrated in the host cell genome to produce stable transformants. Techniques for introducing vectors into eukaryotic cells and techniques for selecting stable transformants using a dominant selectable marker are described, for example, by Ausubel (1990, 1995) and by Murray, supra.

Expression vectors can also be introduced into plant protoplasts, intact plant tissues, or isolated plant cells. General methods of culturing plant tissues are provided, for example, by Miki et al., "Procedures for Introducing Foreign DNA into Plants," in *Methods in Plant Molecular Biology and Biotechnology*, Glick et al. (eds.), pages 67–88 (CRC Press, 1993). Methods of introducing expression vectors into plant tissue include the direct infection or co-cultivation of plant tissue with *Agrobacterium tumefaciens*. Horsch et al., *Science* 227:1229 (1985). Descriptions of Agrobacterium vector systems and methods for Agrobacterium-mediated gene transfer are provided by Gruber et al., "Vectors for Plant Transformation," in *Methods in Plant Molecular Biology and Biotechnology*, Glick et al. (eds.), pages 89–119 (CRC Press 1993), Miki et al., supra, and Moloney et al., *Plant Cell Reports* 8:238 (1989).

Alternatively, expression vectors are introduced into plant tissues using a direct gene transfer method such as microprojectile-mediated delivery, DNA injection, electroporation, and the like (see, for example, Gruber et al., supra; Miki et al., supra; Klein et al., *Biotechnology* 10:268, 1992). For example, expression vectors can be introduced into plant tissues using microprojectile-mediated delivery with a biolistic device (see, generally, Yang and Christou (eds.), *Particle Bombardment Technology for Gene Transfer* (Oxford University Press 1994)).

5. Isolation of Cloned UDPGdH Enzymes, Measurement of Enzyme Activity, and Production of Anti-UDPGdH Antibodies (a) Isolation of Protein Expressed by Cloned UDPGdH Genes General methods for recovering protein produced by a recombinant host are well-known to those of skill in the art. For example, standard techniques for isolation of protein from a bacterial system are provided by Grisshammer et al., "Purification of over-produced proteins from *E. coli* cells," in *DNA Cloning 2: Expression Systems*, 2nd Edition, Glover et al. (eds.), pages 59–92 (Oxford University Press 1995); Georgiou, "Expression of Proteins in Bacteria," in *Protein Engineering: Principles and Practice*, Cleland et al. (eds.), pages 101–127 (Wiley-Liss, Inc. 1996). Moreover, well-known methods for isolating protein from both bacterial and yeast systems are described by Wu et al., "Large-Scale Expression and Purification of Recombinant Proteins in Cultured Cells," in *Methods in Gene Biotechnology*, pages 368–398 (CRC Press 1997). Established techniques for isolating recombinant proteins from a baculovirus system are described by Richardson (ed.), *Baculovirus Expression Protocols* (The Humana Press, Inc. 1995).

More generally, UDPGdH protein can be isolated by standard techniques, such as affinity, chromatography, size exclusion chromatography, ionic exchange chromatography, HPLC and the like. For example, Robertson et al., *Biochem. J.* 313:311 (1996), describe a method for purifying to homogeneity French bean UDPGdH using hydrophobic-interaction chromatography, gel filtration, and dye-ligand chromatography. Additional variations in enzyme isolation and purification can be devised by those of skill in the art. For example, anti-UDPGdH antibodies, obtained as described below, can be used to isolate large quantities of enzyme by immunoaffinity purification.

Isolated UDPGdH protein, obtained from recombinant hosts, can be used to produce polysaccharide precursors in vitro. Moreover, UDPGdH from cloned UDPGdH genes is useful for the stereospecific production of UDP-D-glucuronic acid as a fine chemical. For example, a preparation of isolated polypeptide having UDPGdH enzyme activity can be used to synthesize stereospecifically-labeled tritiated UDP-D-glucuronic acid. In a similar manner, isolated polypeptides having mutant UDPGdH enzyme activity are useful for synthesis of stereospecifically-labeled UDP-6-aldehydo-D-glucose.

(b) Assays for Variant and Mutant UDPGdH Enzymes

UDPGdH enzyme activity can be determined by measuring the rate of change of absorbance at 340 nm caused by the reduction of nicotinamide adenine dinucleotide which accompanies the oxidation of UDP-D-glucose to UDP-D- glucuronic acid. Such spectroscopic UDPGdH assays are well-known to those of skill in the art (see, for example, Roberts and Cetorelli, in "UDP-D-glucuronic acid pyrophosphorylase and the formation of UDP-D-glucuronic acid in plants," *Biogenesis of Plant Cell Wall Polysaccharides* (Loewus, ed.), pages 49–68 (Academic Press 1973); Lin et al., *Biochem. Biophys. Res. Commun.* 207:223, 1995; Tenhaken and Thulke, *Plant Physiol.* 112:1127, 1996). Example 4 illustrates the use of such a spectroscopic UDPGdH assay. As an alternative, UDPGdH activity can be measured using a radioenzymatic assay in which the enzyme converts radiolabeled UDP-D-glucose to radiolabeled UDP-D-glucuronic acid.

As described above, the mutant UDPGdH enzyme catalyzes the oxidation of UDP-D-glucose to to the corresponding aldehyde. The overall reaction for the wild-type enzyme is:

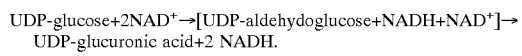

UDP-glucose+2NAD$^+$→[UDP-aldehydoglucose+NADH+NAD$^+$]→ UDP-glucuronic acid+2 NADH.

Since the mutant enzyme cannot catalyze the second half-reaction, the stoichiometry will be one NADH produced for each UDP-D-glucose consumed, whereas the wild-type enzyme produces two NADH/UDP-D-glucose consumed. Accordingly, calculation of moles of NADH produced for a given amount of UDP-D-glucose added to the reaction will indicate the extent to which a mutant enzyme produces UDP-D-aldehydoglucose. The calculation can be performed from Beer's Law:

$$A = \epsilon \cdot c \cdot l$$

where "A" is the measured absorbance, "$\epsilon$" is the molar extinction coefficient (in this case, 6220 cm$^{-1}$·M$^{-1}$), "l" is the path length of the cuvette used, and "c" is the concentration in mol·l$^{-1}$. Alternatively, a radioenzymatic assay can be used to determine mutant UDPGdH activity in which the mutant enzyme converts radiolabeled UDP-D-glucose to radiolabeled UDP-D-aldehydoglucose as the final product. Measurement of both UDP-D-aldehydoglucose and UDP-D-glucuronic acid by either method will indicate the extent to which a mutant UDPGdH enzyme produces any UDP-D-glucuronic acid.

(c) Preparation of Anti-UDPGdH Antibodies and Fragments Thereof

Antibodies to UDPGdH can be obtained, for example, using the product of an expression vector as an antigen. Polyclonal antibodies to recombinant enzyme can be prepared using methods well-known to those of skill in the art (see, for example, Green et al., "Production of Polyclonal Antisera," in *Immunochemical Protocols* (Manson, ed.), pages 1–5 (Humana Press 1992); Williams et al., "Expression of foreign proteins in *E. coli* using plasmid vectors and purification of specific polyclonal antibodies," in *DNA Cloning 2: Expression Systems*, 2nd Edition, Glover et al. (eds.) page 15 (Oxford University Press 1995).

Alternatively, an anti-UDPGdH antibody can be derived from a rodent monoclonal antibody. Rodent monoclonal antibodies to specific antigens may be obtained by methods known to those skilled in the art (see, for example, Kohler et al., *Nature* 256:495, 1975; and Coligan et al. (eds.), *Current Protocols in Immunology*, Vol. 1, pages 2.5.1–2.6.7 (John Wiley & Sons 1991) ["Coligan"]; Picksley et al., "Production of monoclonal antibodies against proteins expressed in *E. coli*," in *DNA Cloning 2: Expression Systems*, 2nd Edition, Glover et al. (eds.), page 93 (Oxford University Press 1995)).

Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1–2.7.12 and pages 2.9.1–2.9.3; Baines et al., "Purification of Immunoglobulin G (IgG)," in *Methods in Molecular Biology*, Vol. 10, pages 79–104 (The Humana Press, Inc. 1992)).

For particular uses, it may be desirable to prepare fragments of anti-UDPGdH antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. Nos. 4,036,945 and 4,331,647 and references contained therein. Also, see Nisonoff et al., *Arch Biochem. Biophys.* 89:230 (1960); Porter, *Biochem. J.* 73:119 (1959), Edelman et al., in *Methods in Enzymology* Vol. 1, page 422 (Academic Press 1967), and Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described in Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437, 1992).

Preferably, the Fv fragments comprise $V_H$ and $V_L$ chains which are connected by a peptide linker. These single-chain antigen binding proteins (sFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology* 2:97 (1991). Also see Bird et al., *Science* 242:423 (1988), Ladner et al., U.S. Pat. No. 4,946,778, Pack et al., *Bio/Technology* 11:1271 (1993), and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (See, for example, Larrick et al., *Methods: A Companion to Methods in Enzymology* 2:106 (1991); Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995)).

6. Modification of Polysaccharide Biosynthesis in Transgenic Plants That Express a Foreign UDPGdH Gene Starch, the major reserve polysaccharide for green plants, is composed of two major polysaccharides: amylose and amylopectin. Starch is synthesized in amyloplasts and stored in the major depots of seeds, tubers, and roots. Starch granules can also be synthesized in the amyloplasts, chloroplasts, and chloroamyloplasts of other tissues.

As mentioned above, starch has many industrial uses including the production use by the food industry, textile manufactures, paper manufacturers, and the pharmaceutical industry, among others. Further, starch is used in the production of industrial alcohol, chemical feedstock, adhesives, and food additives. As a food additive, starch has been used for its gelling properties, but the narrow range of the properties of native starches has been a limitation on its usefulness (see, for example, Galliard and Bowler, in *Starch: Properties and Potential* (Galliard, ed.), page 55 (John Wiley & Sons 1987)).

In order to alter plant polysaccharide biosynthesis, an expression vector is constructed in which a nucleotide sequence encoding a UDPGdH gene is operably linked to nucleotide sequences that regulate gene transcription. The general requirements of an expression vector are described above in the context of a transient expression system. Here, however, the objective is to introduce the expression vector into plant embryonic tissue in such a manner that a UDPGdH enzyme will be expressed in tissues of the adult plant. One method of obtaining mitotic stability is provided by the integration of expression vector sequences into the host chromosome. Such mitotic stability can be provided by the microprojectile bombardment and the Agrobacterium-mediated transformation techniques illustrated in Example 2 and Example 3, respectively.

Transcription of a UDPGdH gene in a transgenic plant can be controlled by a viral promoter, such as a Cauliflower Mosaic Virus (CaMV) promoter and a Figwort Mosaic Virus promoter. Additional useful promoters include ubiquitin promoters, mannopine synthase promoters, DNAJ, GST-responsive promoters, and heat shock gene promoters (e.g., hsp70). Regulatory elements that provide tissue-specific gene expression are also useful. Such regulatory elements include, for example, seed-specific regulatory elements, such as maize zein or waxy regulatory elements, napin regulatory elements (U.S. Pat. No. 5,420,034), cruciferin regulatory elements from canola, helianthinin regulatory elements from sunflower, the α'-conglycinin subunit regulatory elements from soybean, Bce4 regulatory elements (U.S. Pat. No. 5,530,194), or regulatory elements from genes of other seed storage proteins (see, for example, Gruber et al., supra). Additional suitable regulatory elements are well-known to those of skill in the art.

Depending upon the application, it may be desirable to select promoters that are not constitutive but specific for expression in one or more tissues of the plant. Such examples include the light-inducible promoters of the small subunit of ribulose 1,5-bisphosphate carboxylase, if the expression is desired in photosynthetic tissues, or promoters of seed-specific genes, as noted above. In addition, specific timing of expression may be desirable. In this regard, chemically-inducible promoters are known in the art which allow the controlled expression of a gene of interest at a specific stage of development (see, for example, Hershey et al., international publication No. WO 90/11 361).

Particularly preferred regulatory elements and promoters are those that allow seed-specific expression. Examples of seed-specific regulatory elements and promoters include but are not limited to nucleotide sequences that control expression of seed storage proteins, which can represent up to 90% of total seed protein in many plants. The seed storage proteins are strictly regulated, being expressed almost exclusively in seeds in a highly tissue-specific and stage-specific manner (see, for example, Higgins et al., *Ann. Rev. Plant Physiol.* 35:191, 1984; Goldberg et al., *Cell* 56:149, 1989). Moreover, different seed storage proteins may be expressed at different stages of seed development. Expression of seed-specific genes has been studied in great detail (see, for example, Goldberg et al., *Cell* 56:149, 1989; Higgins et al., *Ann. Rev. Plant Physiol.* 35:191, 1984).

As discussed above, this invention provides the expression in plants of a UDPGdH gene under control of a promoter, and optionally, a regulatory element, such as an organelle-specific, cell-specific, or tissue-specific regulatory element. The choice of the promoter and a regulatory element will depend in part upon the desired result.

In certain embodiments, the vector can also contain a reporter gene and UDPGdH. The inclusion of a reporter gene allows determination of transformation and expression. The GUS (β-glucoronidase) gene is preferred (see, for example, U.S. Pat. No. 5,268,463). Other reporter genes, such as β-galactosidase, luciferase, green fluorescent protein, and the like, are also suitable in the context of this invention. Methods and substrates for assaying expression of each of these genes are well known in the art. The reporter gene should be under control of a promoter that is functional in plants. Such promoters include CaMV 35S promoter, mannopine synthase promoter, ubiquitin promoter and DNA J promoter.

Particular uses for UDPGdH expression may require additional regulatory elements, as discussed below. For example, an expression vector can include a nucleotide sequence that encodes a transit peptide joined with UDPGdH-encoding sequences. Transit peptides enable the translocation of a nuclear encoded polypeptide into the chloroplast or the mitochondria, the lumen of the endoplasmatic reticulum or other cellular compartments. During the translocation process, the transit peptide is separated or proteolytically removed from the protein or subunit. Plant transit sequences are well-known in the art (see, for example, Keegstra and Olsen, *Annu. Rev. Plant Mol. Biol.* 40:471, 1989).

As an illustration, the transit peptide of the small subunit of the enzyme 1,5-ribulose bisphosphate carboxylase enables transport into chloroplasts. This peptide and other chloroplast transit peptides can also be used in the present invention (see, for example, Krebbers et al., *Plant Mol. Biol.* 11:745, 1988; European patent application No. 85402596.2; Watson, *Nucl. Acids Res.* 12:5145, 1984; Yon Heijne et al., *Plant Mol. Biol. Rep.* 9:104, 1991). Suitable mitochondrial targeting peptides include the mitochondrial transit peptides described by Schatz, *Eur. J. Biochem.* 165:1 (1987), and listed by Watson, supra. Suitable targeting peptides that can translocate a protein of interest to the lumen of the endoplasmatic reticulum of a plant cell include, for example, the signal peptides described by Von Heijne, *Biochem. Biophys. Acta* 947:307 (1988), and by Watson, supra.

In general, transit peptide sequences obtained from any polypeptide that is transported into plastids can be used to direct the UDPGdH gene product to the desired subcellular compartment. Preferred transit peptides include sequences associated with the following genes: brittle-1, small subunit ot ribulose 1,5-bisphospate carboxylase, and light harvesting chlorophyll protein. Suitable amino acid sequences of transit peptides are well-known to those of skill in the art (see, for example, Sullivan et al., *Plant Cell* 3:1337, 1991; Gosh et al., *Photochem. Photobiol.* 57:352, 1993; Gotor et al., *Plant J.* 3:509, 1993; Sullivan, *Planta* 196:477, 1995; Pear et al., *Proc. Nat'l Acad. Sci. USA* 93:12637, 1996).

For example, the transit peptide sequence of the brittle-1 gene, which directs the associated polypeptide into amyloplasts, is described by Sullivan et al., *Plant Cell* 3:1337 (1991), and by Li et al., *Journal of Biological Chemistry* 267:18999 (1992). A suitable brittle-1 transit peptide is encoded by the following nucleotide sequence which includes additional amino acids (encoded by nucleotides 226–237) to preserve protease cleavage junction integrity:

plants include barley, maize, oat, wheat, sorghum, rice, soybean, canola, sunflower and the like.

(a) Use of UDPGdH Genes to Modify the Characteristics of Plant Starch

In one embodiment of the present invention, a UDPGdH gene is expressed in endosperm amyloplasts to provide UDP-D-glucuronic acid as an alternative substrate for starch synthases in order to produce carboxylated starch. Carboxylated starch can be used in place of phosphorylated starch. Since the pKa of the carboxylate anion is lower than that of the bound phosphate group, carboxylated starch is superior to phosphorylated starch in many uses. For example, carboxylated starch can be used in food where a negative charge at pH 5.0–5.5 is desired. Suitable UDPGdH genes for the production of carboxylated starch include the maize UDPGdH gene disclosed herein, as well as variants of the maize UDPGdH genes. Standard methods, such as commercial wet milling methods, can be used to isolate carboxylated starch from plants.

Alternatively, expression of a mutant UDPGdH gene in endosperm amyloplasts will provide a source of aldehydic starch. This is so because mutant UDPGdH enzymes oxidize UDP-D-glucose to UDP-6-aldehydo-D-glucose, which can serve as a substrate for starch synthases. Currently, chemically-synthesized aldehydic starch is used as a superior fiber cross-linking molecule (a flocculating agent) in the wet-end of paper manufacture. The mutant UDPGdH genes of the present invention provide a means to synthesize aldehydic starch in vivo.

```
  1 ATGGCGGCGA CAATGGCAGT GACGACGATG GTGACCAGGA GCAAGGAGAG[SEQ ID NO:5]

51 CTGGTCGTCA TTGCAGGTCC CGGCGGTGGC ATTCCCTTGG AAGCCACGAG

101 GTGGCAAGAC CGGCGGCCTC GAGTTCCCTC GCCGGGCGAT GTTCGCCAGC

151 GTCGGCCTCA ACGTGTGCCC GGGCGTCCCG GCGGGGCGCG ACCCGCGGGA

201 GCCCGATCCC AAGGTCGTCC GGGCGGCCGA CCTCATG.
```

In order to select transformed cells, an expression vector can contain a selectable marker gene, such as a herbicide resistance pene or an antibiotic resistance gene. For example, such genes may confer resistance to phosphinothricin, glyphosate, sulfonylureas, atrazine, imidazolinone or aminoglycoside antibiotics such as neomycin, kanamycin and G418 (genticin). Preferred selectable marker genes are the neomycin phosphotransferase gene (nptII gene), and the bar gene or pat gene which encodes phosphinothricinacetyltransferase. The nucleotide sequences of bar genes can be found in Leemans et al., European patent application No. 0-242-246 (1987), and in White et al., *Nucleic Acids Res.* 18: 1062 (1990). Wohlleben et al., *Gene* 70: 25 (1988), disclose the nucleotide sequence of the pat gene. Bar or pat gene expression confers resistance to herbicides such as glufosinate (sold as Basta® and Ignite®, among others) and bialaphos (sold as Herbi-ace® and Liberty®).

The expression vector can contain nucleotide sequences encoding a UDPGdH protein under the control of a regulatory element, as well as the selectable marker gene under control of a constitutive promoter. Alternatively, the selectable marker gene can be delivered to host cells in a separate selection expression vector by co-transformation with both vectors.

Any plant that would benefit from either expression of a UDPGdH gene or inhibition of UDPGdH activity is suitable for transformation within the context of this invention. Such As described above, UDPGdH polypeptide can be directed into subcellular compartments using transit peptide sequences. Suitable transit peptide sequences are well-known in the art (see, for example, Keegstra and Olsen, *Annu. Rev. Plant Mol. Biol.* 40:471, 1989). For example, suitable transit peptide sequences for translocating UDPGdH or mutant UDPGdH into endosperm amyloplasts include transit peptide sequences from small subunit of ribulose 1,5-bisphosphate carboxylase gene, chlorophyll a/b binding protein gene, and the brittle-1 gene. A preferred transit peptide sequence is obtained from the brittle-1 gene.

It may be advantageous to suppress endogenous UDPGdH activity to provide suitable levels of mutant UDPGdH enzyme activity. Such suppression can be achieved by methods well known in the art, for example, by inducing homologous recombination into the nucleotide sequence of the endogenous gene.

(b) Use of UDPGdH Genes to Enhance Expression of UDPGdH Enzyme Activity in Transgenic Plants Pectin polysaccharides are heterogeneous, branched, and highly hydrated polysaccharides. Pectins are present in the primary cell walls of all seed-bearing plants and are located particularly in the middle lamella (see, for example, Bacic et al., in *The Biochemistry of Plants* (Preiss, ed.), 14:297 (Academic Press 1988)). Hemicellulosic polysaccharides are a heterogenous group of branched matrix polysaccharides that bind tightly but noncovalently to the surface of the cellulose microfibrils and to each other. Those polysaccharides associated with the hemicellulosic fraction include glucans, xylans, xyloglucans, and the mannans. Hemicelluloses are present in both the primary and secondary cell wall of plants. For example, xylans are major components of the walls of monocots, representing about 20% of each of the primary and secondary walls. In dicots, xylans compose about 20% of the secondary cell wall, but only 5% of the primary cell wall. Additional exudate gums are derived from precursors generated by UDPGdH (see, for example, Stephen et al., in *Methods in Plant Biochemistry* (Dey and Harborne, eds.) 2:483 (1990). Since UDPGdH plays a central role in the generation of precursors for pectic and hemicellulosic substances as well as exudate gums, regulation of this enzyme has a significant effect on the formation of the plant cell wall.

In one embodiment of the present invention, a UDPGdH gene is over-expressed in the cytosol to increase gum production. It is well known in the art that a variety of commercial gums and certain maize hemicellulosic substances have useful rheological properties. The concentration of these gums in wet milling streams is low thus relegating them to co-product status rather than principal product status. In other systems, UDPGdH is central and rate-limiting in the production of gums (see, for example, Aarrecubieta et al., *Gene* 167(1-2):1, 1995); Lin et al., *Biochem. Biophys. Res. Comm.* 207:223, 1995); Robertson et al., *Biochem. J.* 306:745, 1995); Witt, *J. Plant Phys.* 140:276, 1992). The maize UDPGdH gene and variants thereof are useful for over-expression of UDPGdH enzyme activity, leading to high gum production.

Suitable expression vectors for increasing gum production include regulatory elements, promoters, and transit peptide-encoding sequences that enhance UDPGdH activity in seeds. As an illustration, a portion of the celA gene can provide a transit peptide-encoding nucleotide sequence that directs exogenous UDPGdH activity to aleurone cells of seeds.

In a further embodiment, over-expression of UDPGdH in the pericarp may lend enhanced structural strength to the pericarp. Since hemicellulogic and pectic substances play a key role in cell wall integrity, UDPGdH genes of the present can be used to provide plants with strengthened cell walls. Stronger cell walls, in turn, are effective in reducing the susceptibility to a variety of insects and pathogens. For example, over-expression in roots may lead to reduced feeding by root worms.

Over-expression of the UDPGdH polypeptide can be achieved by inserting the nucleotide sequence identified by SEQ ID NO:1, SEQ ID NO:3, or a variant thereof, into an expression vector with a strong promoter. In one such example, the CaMV 35S promoter can be used to direct strong constitutive expression of a nucleotide sequence operably linked thereto. Preferred regulatory elements for endosperm expression include regulatory elements of γ-zein, α-zein, and waxy genes. Pericarp-specific expression can be achieved, for example, by using regulatory elements of the celA gene. Root-specific expression can be achieved, for example, by using the regulatory element of the wheat peroxidase gene.

(c) Use of UDPGdH Gene Sequence tag Inhibit Expression of UDPGdH Enzyme Activity in Transgenic Plants The present invention also contemplates methods for the suppression of endogenous UDPGdH expression. Such diminished expression offers advantages in industry and in agriculture. The inhibition of UDPGdH gene expression in maize seeds, for example, will enhance starch production from corn used in the wet milling industry. Briefly, the wet milling process produces various mass streams, including a starch fraction, a germ fraction, a gluten feed fraction, and a gluten meal fraction. The gluten feed fraction has a large amount of fine fiber associated with starch. Since the ratio of starch to fine fiber is essentially invariant, a reduction in the amount of fine fiber in the gluten feed fraction will reduce the amount of starch co-partitioning in that fraction. Consequently, a reduction in fine fiber, caused by decreased UDPGdH activity, will increase the amount of starch that partitions into the starch stream.

Another benefit of decreasing UDPGdH activity is that by lowering the amount of hemicelluolose materials in the endosperm or the pericarp there will be a diminution of cell wall strength in the endosperm. As a result, less effort will be required to break cells open and to recover starch during the wet milling process. Moreover, one could achieve the same grinding efficiency with such plant material using lesser steep times.

In addition to improving plant material used in wet milling processes, an inhibition of UDPGdH provides an improved grain used as animal feed. This is so because a diminished production of hemicelluloses in stalk, resulting from decreased UDPGdH activity, leads to diminished cross-linking of hemicellulose and lignin, which may enhance the value of the stover for silage. Similarly, a diminution in hemicellulosic substances enhances the value of grain. A diminished expression of UDPGdH and the concomitant decrease in hemicelluloses also results in increased amino acid availability, increased metabolizable energy, and reduced nitrogenous wastes. As a counter-example, the addition of alkali extracted cell wall materials (the hallmark of hemicellulosic polymers, see Selvendran and Ryden, in *Methods in Plant Biochemistry* (Dey and Harborne, eds.) 2:549–579, 1990) added back to the diet of broiler chickens diminished the digestibility of protein and lipid (Smits and Annison, *World's Poultry Science J.* 52:203, 1996).

The repression of endogenous UDPGdH gene expression can be accomplished by techniques well known in the art. A preferred method of inhibiting expression of endogenous UDPGdH is to take advantage of co-suppression. Homology-dependent gene silencing, or co-suppression, is a phenomenon in which the expression of a transgene (or, "exogenous gene") and the expression of an endogenous gene are inhibited (see, for example, Taylor, *The Plant Cell* 9:1245, 1997). Those of skill in the art are aware that a certain percentage of transgenic plants that contain such an expression vector will exhibit either trait. For example, about 2 to 28% of transgenic plants that contain a vector expressing a protein that is also endogenously produced may exhibit the co-suppression phenotype, while other transgenic plants will contain cells that over-express the protein.

Standard techniques of using co-suppression to inhibit expression of plant genes are well-known to those of skill in the art (see, for example, Meyer and Saedler, *Annu. Rev. Plant Physiol. Plant Mol. Biol.* 47:23, 1996; Depicker and Van Montagu, *Curr. Opin. Cell Biol.* 9:373, 1997; Jorgensen and Napoli, U.S. Pat. No. 5,034,323 (1991): Ebbers et al., U.S. Pat. No. 5,231,010 (1993); Jorgensen and Napoli, U.S. Pat. No. 5,283,184 (1994)). Co-suppression can be achieved using a vector that expresses a complete polypeptide or using a vector that expresses only a short sense fragment. For example, Palauqui and Vaucheret, *Plant Molecular Biology* 29:149 (1995), have shown that co-suppression can be induced using fragments that lack the 3' untranslated region or the 5' untranslated region of a gene. On the other hand, Cammeron and Jennings, *Nucleic Acids Res.* 19:469

(1991), demonstrated that co-suppression can be achieved using only 28 bases of the 5' untranslated region with 70 bases of the coding sequence.

In the present context, therefore, endogenous UDPGdH expression can be inhibited by introducing a nucleic acid molecule that encodes at least part of the UDPGdH gene. For example, co-suppression may be achieved using a vector that expresses 70 bases of a UDPGdH gene. Regardless of whether a vector expresses a complete UDPGdH sequence or a UDPGdH fragment, the co-suppression phenotype of plant cells can be identified using a UDPGdH enzyme assay, as described herein. Such enzyme assays will identify transgenic plants that exhibit the co-suppression phenotype, and that are suitable for further breeding of plants having reduced UDPGdH enzyme activity.

Alternatively, anti-sense technology can be conveniently used (see, for example, Sheehy et al., *Proc. Nat'l Acad. Sci. USA* 85:8805, 1988); Hiatt et al., U.S. Pat. No. 4,801,340). The binding of anti-sense RNA molecules to target mRNA molecules results in hybridization arrest of translation (see, for example, Paterson, et al., *Proc. Nat'l Acad. Sci. USA*, 74: 4370, 1987). Anti-sense RNA has been used to inhibit plant target genes in a dominant and tissue-specific manner (see, for example, Van der Krol et al., *Gene* 72:45, 1988; Ecker et al., *Proc. Nat'l Acad. Sci. USA* 83:5372, 1986; Van der Krol et al., *Nature* 336:866, 1988; Smith et al., *Nature* 334:724, 1988); Sheehy et al., *Proc. Nat'l Acad. Sci. USA* 85:8805, 1988; Rothstein et al., *Proc. Nat'l Acad. Sci. USA* 84:8439, 1987; Cornelissen et al., *Nucl. Acids Res.* 17:833, 1988); Cornelissen, *Nucl. Acid Res.* 17:7203, 1989; Robert et al., *Plant Mol. Biol.* 13:399, 1989).

Anti-sense inhibition of the endogenous gene can be effected, for example, by introducing into a plant an expression vector having a plant promoter operably linked to a DNA molecule of at least 20 base pairs derived from a UDPGdH-encoding nucleotide sequence, in which the DNA molecule is linked to the promoter in the opposite orientation for expression. By inhibiting the synthesis of the enzyme, the conversion of UDP-D-glucose to UDP-D-glucuronic acid can be diminished, thereby decreasing the production of hemicellulosic polymers.

The origin of the promoter used to drive the expression of anti-sense RNA is not critical as long as it has sufficient transcriptional activity to accomplish the invention by decreasing the level of translatable UDPGdH mRNA in the host cells. Preferred promoters include strong constitutive plant promoters, such as those directing the 19S and 35S transcripts in cauliflower mosaic virus and tissue or developmentally-specific promoters such as those for the small subunit of ribulose 1,5-bisphosphate carboxylase, maize α-zein protein, maize γ-zein protein, and chlorophyll a/b binding protein (see, for example, Odell et al., *Nature* 313:810, 1985; Hull and Howell, *Virology* 86:482, 1987; Morelli et al., *Nature* 315:200, 1985; Broglie et al., *Science* 224:838, 1984; Hererra-Estrella et al., *Nature* 310:115, 1984; Coruzzi et al., *EMBO J.* 3:1671, 1984; Faciotti et al., *Bio/Technology* 3:241, 1985; Matzke et al., *EMBO J.* 3:1525, 1984; Lampa et al., *Nature* 316:750, 1986).

Alternatively, an expression vector can be constructed in which a regulatory element is operably linked to a nucleotide sequence that encodes a ribozyme. Ribozymes can be designed to express endonuclease activity that is directed to a certain target sequence in a mRNA molecule. For example, Steinecke et al., *EMBO J.* 11: 1525 (1992), achieved up to 100% inhibition of neomycin phosphotransferase gene expression by ribozymes in tobacco protoplasts. Similarly, Perriman et al., *Antisense Research and Development* 3: 253 (1993), inhibited chloramphenicol acetyl transferase activity in tobacco protoplasts using a vector that expressed a modified hammerhead ribozyme. In the context of the present invention, ribozymes include nucleotide sequences that bind with UDPGdH mRNA. Suitable sequences can be derived from the nucleotide sequence of the maize UDPGdH genes, described herein.

In a further alternative approach, expression vectors can be constructed in which a regulatory element directs the production of RNA transcripts capable of promoting RNase P-mediated cleavage of UDPGdH mRNA molecules. According to this approach, an external guide sequence can be constructed for directing the endogenous ribozyme, RNase P, to a particular species of intracellular mRNA, which is subsequently cleaved by the cellular ribozyme (see, for example, Altman et al., U.S. Pat. No. 5,168,053; Yuan et al., *Science* 263:1269, 1994). Preferably, the external guide sequence comprises a ten to fifteen nucleotide sequence complementary to UDPGdH mRNA, and a 3'-NCCA nucleotide sequence, wherein N is preferably a purine. Id. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region. Id.

Finally, those of skill in the art will recognize that nucleotide sequences encoding single-chain antibodies directed toward endogenous UDPGdH can be inserted into expression vectors and introduced into host cells. Upon expression, the endogenous UDPGdH protein will be rendered inactive by antibody binding.

The present invention, thus generally described, will be understood more readily by reference to the following examples, which are provided by way of illustration and are not intended to be limiting of the present invention.

EXAMPLE 1

ISOLATION OF MAIZE UDPGDH GENES

Total RNA was isolated from maize tissues with TRIzol Reagent (Life Technologies Inc., Gaithersburg, Md.) using a modification of the guanidine isothiocyanate/acid-phenol procedure described by Chomczynski and Sacchi, *Anal. Biochem.* 162:156 (1987). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

The selection of poly(A)+ RNA from total RNA was performed using PolyATact system (Promega Corporation, Madison, Wis.). Briefly, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water. cDNA synthesis was performed and unidirectional cDNA libraries were constructed using the SuperScript Plasmid System (Life Technologies Inc., Gaithersburg, Md). The first stand of cDNA was synthesized by priming an oligo(dT) primer containing a NotI site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between NotI and SalI sites. Individual colonies were picked and DNA was prepared either by PCR with M13 forward primers and M13 reverse primers, or by plasmid miniprep isolation. All the cDNA clones were sequenced using M13 reverse primers. cDNA clones containing UDPGdH-encoding sequences were identified using a Basic Local Alignment Search Tool (BLAST) program.

EXAMPLE 2

INTRODUCTION OF A MAIZE UDPGdH GENE INTO PLANTS BY MICROPARTICLE BOMBARDMENT

Transgenic maize plants can be produced by bombardment of embryogenically responsive immature embryos with tungsten particles associated with plasmids. The plasmids consist of a selectable gene and a UDPGdH gene.

(a) Preparation of Microparticles

Fifteen milligrams of tungsten particles (General Electric), 0.5 to 1.8$\mu$ in diameter, preferably 1 to 1.8$\mu$, and most preferably 1$\mu$, are added to 2 ml of concentrated nitric acid. This suspension is sonicated at 0° C. for 20 minutes (Branson Sonifier Model 450, 40% output, constant duty cycle). Tungsten particles are pelleted by centrifugation at 10,000 rpm (Biofuge) for one minute, and then supernatant is removed. Two milliliters of sterile distilled water are added to the pellet, and brief sonication is used to resuspend the particles. The suspension is pelleted, one milliliter of absolute ethanol is added to the pellet, and brief sonication is used to resuspend the particles. Rinsing, pelleting, and resuspending of the particles is performed two more times with sterile distilled water, and finally the particles are resuspended in two milliliters of sterile distilled water. The particles are subdivided into 250-ml aliquots and stored frozen.

To coat particles with plasmid DNA, the stock of tungsten particles is sonicated briefly in a water bath sonicator (Branson Sonifier Model 450, 20% output, constant duty cycle) and 50 $\mu$l are transferred to a microfuge tube. Equimolar amounts of plasmid DNA encoding a selectable gene and a UDPGdH gene are added to the particles for a final DNA amount of 0.1 to 10 $\mu$g in 10 $\mu$l total volume, and briefly sonicated. Preferably, 1 $\mu$g total DNA is used. Specifically, aliquots of an expression vector comprising the bar gene and an expression vector comprising a UDPGdH gene, both at 0.1 mg/ml in TE buffer, are added to the particle suspension. Fifty microliters of sterile aqueous 2.5 M CaCl$_2$ are added, and the mixture is briefly sonicated and vortexed. Twenty microliters of sterile aqueous 0.1 M spermidine are then added and the mixture is briefly sonicated and vortexed. The mixture is incubated at room temperature for 20 minutes with intermittent brief sonication. The particle suspension is centrifuged, and the supernatant is removed. Two hundred fifty microliters of absolute ethanol are added to the pellet, followed by brief sonication. The suspension is pelleted, the supernatant is removed, and 60 ml of absolute ethanol are added. The suspension is sonicated briefly before loading the particle-DNA aglomeration onto macrocarriers.

(b) Bombardment of Maize Tissue

Immature embryos of maize variety High Type II are a suitable target for particle bombardment-mediated transformation. This genotype is the F$_1$ of two purebred genetic lines, parents A and B, derived from the cross of two known maize inbreds, A188 and B73. Both parents were selected for high competence of somatic embryogenesis, according to Armstrong et al., *Maize Genetics Coop. News* 65:92 (1991).

Ears from F$_1$ plants are selfed or sibbed, and embryos are aseptically dissected from developing caryopses when the scutellum first becomes opaque. This stage occurs about 9–13 days post-pollination, and most generally about 10 days post-pollination, depending on growth conditions. The embryos are about 0.75 to 1.5 millimeters long. Ears are surface-sterilized with 20–50% Clorox for 30 minutes, followed by three rinses with sterile distilled water.

Immature embryos are cultured with the scutellum oriented upward, on embryogenic induction medium comprised of N6 basal salts, Eriksson vitamins, 0.5 mg/l thiamine HCl, 30 gm/l sucrose, 2.88 gm/l L-proline, 1 mg/l 2,4-dichlorophenoxyacetic acid, 2 gm/l Gelrite, and 8.5 mg/l silver nitrate (see, for example, Chu et al., *Sci. Sin.* 18:659, 1975; Eriksson, *Physiol. Plant* 18:976, 1965). The medium is sterilized by autoclaving at 121° C. for 15 minutes and dispensed into 100×25 mm Petri dishes. Silver nitrate is filter-sterilized and added to the medium after autoclaving. The tissues are cultured in complete darkness at 28° C. After about 3 to 7 days, most usually about 4 days, the scutellum of the embryo has swelled to about double its original size and the protuberances at the coleorhizal surface of the scutellum indicates the inception of embryogenic tissue. Up to 100% of the embryos may display this response, but most commonly, the embryogenic response frequency is about 80%.

When the embryogenic response is observed, the embryos are transferred to a medium comprised of induction medium modified to contain 120 gm/l sucrose. The embryos are oriented with the coleorhizal pole, the embryogenically responsive tissue, upwards from the culture medium. Ten embryos per Petri dish are located in the center of a Petri dish in an area about 2 cm in diameter. The embryos are maintained on this medium for 3–16 hour, preferably 4 hours, in complete darkness at 28° C. just prior to bombardment with particles associated with plasmid DNAs containing selectable marker and UDPGdH genes.

To effect particle bombardment of embryos, the particle-DNA agglomerates are accelerated using a DuPont PDS-1000 particle acceleration device. The particle-DNA agglomeration is briefly sonicated and 10 $\mu$l are deposited on macrocarriers and the ethanol is allowed to evaporate. The macrocarrier is accelerated onto a stainless-steel stopping screen by the rupture of a polymer diaphragm (rupture disk). Rupture is effected by pressurized helium. The velocity of particle-DNA acceleration is determined based on the rupture disk breaking pressure. Rupture disk pressures of 200 to 1800 psi can be used, with 650 to 1100 psi being preferred, and about 900 psi being most highly preferred. Multiple disks are used to effect a range of rupture pressures.

The shelf containing the plate with embryos is placed 5.1 cm below the bottom of the macrocarrier platform. To effect particle bombardment of cultured immature embryos, a rupture disk and a macrocarrier with dried particle-DNA agglomerates are installed in the device. The He pressure delivered to the device is adjusted to 200 psi above the rupture disk breaking pressure. A Petri dish with the target embryos is placed into the vacuum chamber and located in the projected path of accelerated particles. A vacuum is created in the chamber, preferably about 28 inches mercury. After operation of the device, the vacuum is released and the Petri dish is removed.

Bombarded embryos remain on the osmotically-adjusted medium during bombardment, and 1 to 4 days subsequently.

The embryos are transferred to selection medium comprised of N6 basal salts, Eriksson vitamins, 0.5 mg/l thiamine HCl, 30 gm/l sucrose, 1 mg/l 2,4-dichlorophenoxyacetic acid, 2 gm/l Gelrite, 0.85 mg/l silver nitrate, and 3 mg/l bialaphos (Herbiace, Meiji). Bialaphos was added filter-sterilized. The embryos are subcultured to fresh selection medium at 10 to 14 day intervals. After about 7 weeks, embryogenic tissue, putatively transformed for both selectable marker genes and UDPGdH genes, proliferate from about 7% of the bombarded embryos. Putative transgenic tissue is rescued, and that tissue derived from individual embryos is considered to be an event and was propagated independently on selection medium. Two cycles of clonal propagation are achieved by visual selection for the smallest contiguous fragments of organized embryogenic tissue.

A sample of tissue from each event is processed to recover DNA. The DNA is cleaved with a restriction endonuclease and probed with primer sequences designed to amplify DNA sequences overlapping the UDPGdH and non-UDPGdH portion of the plasmid. Embryogenic tissue with amplifiable sequence is advanced to plant regeneration.

For regeneration of transgenic plants, embryogenic tissue is subcultured to a medium comprising MS salts and vitamins (Murashige and Skoog, *Physiol. Plant* 15:473, 1962), 100 mg/l myo-inositol, 60 gm/l sucrose, 3 gm/l Gelrite, 0.5 mg/l zeatin, 1 mg/l indole-3-acetic acid, 26.4 ng/l cis-trans-abscissic acid, and 3 mg/l bialaphos in 100×25 mm Petri dishes, and is incubated in darkness at 28° C. until the development of well-formed, matured somatic embryos can be seen. This requires about 14 days. Well-formed somatic embryos were opaque and cream-colored, and are comprised of an identifiable scutellum and coleoptile. The embryos are individually subcultured to a germination medium comprising MS salts and vitamins, 100 mg/l myo-inositol, 40 gm/l sucrose and 1.5 gm/l Gelrite in 100×25 mm Petri dishes and incubated under a 16 hour light:8 hour dark photoperiod and 40 $\mu$einsteinsm$^{-2}$sec$^{-1}$ from cool-white fluorescent tubes. After about 7 days, the somatic embryos have germinated and produced a well-defined shoot and root. The individual plants are subcultured to germination medium in 125×25 mm glass tubes to allow further plant development. The plants are maintained under a 16 hour light:8 hour dark photoperiod and 40 $\mu$einsteinsm$^{-2}$sec$^{-1}$ from cool-white fluorescent tubes. After about 7 days, the plants are well-established and are transplanted to horticultural soil, hardened off, and potted into commercial greenhouse soil mixture and grown to sexual maturity in a greenhouse. An elite inbred line is used as a male to pollinate regenerated transgenic plants.

EXAMPLE 3

IINTRODUCTION OF THE MAIZE UDPGDH (ZMUDPGDH1) GENE INTO PLANTS BY AGROBACTERIUM TRANSFORMATION (a) Transformation of Hi-II callus Agrobacterium was streaked out from a −80° C. frozen aliquot onto a plate containing PHJ-L medium and cultured at 28° C. in the dark for 3 days. PHJ-L media comprised 25 ml/l Stock Solution A, 25 mill Stock Solution B, 450.9 ml/l Stock Solution C and spectinomycin (Sigma Chemicals, St. Louis, Mo.) added to a concentration of 50 mg/l in sterile ddH$_2$O (stock solution A: K$_2$HPO$_4$ 60.0 g/l, NaH$_2$PO$_4$ 20.0 g/l, adjust pH to 7.0 with KOH and autoclave; stock solution B: NH$_4$Cl 20.0 g/l, MgSO$_4$.7H$_2$O 6.0 g/l, KCl 3.0 g/l, CaCl$_2$ 0.20 g/l, FeSO$_4$.7H$_2$O 50.0 mg/l, autoclave; stock solution C: glucose 5.56 g/l, agar 16.67 g/l (#A-7049, Sigma Chemicals, St. Louis, Mo.) and autoclave). A single colony was picked from the master plate and streaked onto a plate containing PHI-M medium [yeast extract (Difco) 5.0 g/l; peptone (Difco) 10.0 g/l; NaCl 5.0 g/l; agar (Difco) 15.0 g/l; pH 6.8, containing 50 mg/L spectinomycin] and incubated at 28° C. in the dark for 2 days.

Five ml of either PHI-A, [CHU (N6) basal salts (Sigma C-1416) 4.0 g/l, Eriksson's vitamin mix (1000×, Sigma-1511) 1.0 ml/l; thiamine.HCl 0.5 mg/l (Sigma); 2,4-dichlorophenoxyacetic acid (2,4-D, Sigma) 1.5 mg/l; L-proline (Sigma) 0.69 g/l; sucrose (Mallinckrodt) 68.5 g/l; glucose (Mallinckrodt) 36.0 g/l; pH to 5.2] for the PHI basic medium system, or PHI-I [MS salts (GIBCO BRL) 4.3 g/l; nicotinic acid (Sigma) 0.5 mg/l; pyridoxine.HCl (Sigma) 0.5 mg/l; thiamine.HCl 1.0 mg/l; myo-inositol (Sigma) 0.10 g/l; vitamin assay casamino acids (Difco Lab) 1.0 g/l; 2, 4-D 1.5 mg/l; sucrose 68.50 g/l; glucose 36.0 g/l; adjust pH to 5.2 with KOH and filter-sterilize] for the PHI combined medium system and 5 $\mu$l of 100 mM 3'-5-dimethoxy-4'-hydroxyacetophenone (Aldrich Chemicals) were added to a 14 ml Falcon tube in a hood. About 3 full loops (5 mm loop size) Agrobacterium were collected from the plate and suspended in the tube, then the tube was vortexed to make an even suspension. One ml of the suspension was transferred to a spectrophotometer tube and the OD of the suspension was adjusted to 0.72 at 550 nm by adding either more Agrobacterium or more of the same suspension medium. The Agrobacterium concentration was approximately 1×10$^9$ cfu/ml. The final Agrobacterium suspension was aliquoted into 2 ml microcentrifuge tubes, each containing 1 ml of the suspension. The suspensions were then used as soon as possible.

About two milliliters of the same medium (PHI-A or PHI-I) used for the Agrobacterium suspension were added into a 2 ml microcentrifuge tube. Immature embryos were isolated from a sterilized ear with a sterile spatula (Baxter Scientific Products S1565) and dropped directly into the medium in the tube. A total of about 100 embryos were placed in the tube. The optimal size of the embryos was about 1.0–1.2 mm. The cap was then closed on the tube and the tube was vortexed with a Vortex Mixer (Baxter Scientific Products S8223-1) for 5 seconds at maximum speed. The medium was removed and 2 ml of fresh medium were added and the vortexing repeated. All of the medium was drawn off and 1 ml of Agrobacterium suspension was added to the embryos and the tube vortexed for 30 seconds. The tube was allowed to stand for 5 minutes in the hood. The suspension of Agrobacterium and embryos was poured into a Petri plate containing either PHI-B medium [CHU(N6) basal salts (Sigma C-1416) 4.0 g/l; Eriksson's vitamin mix (1000×, Sigma-1511) 1.0 ml/l; thiamine.HCl 0.5 mg/I; 2.4-D 1.5 mg/l; L-proline 0.69 g/l; silver nitrate 0.85 mg/l; Geirite (Sigma) 3.0 g/l; sucrose 30.0 g/l; acetosyringone 100 $\mu$M; pH 5.8], for the PHI basic medium system, or PHI-J medium [MS Salts 4.3 g/l; nicotinic acid 0.50 mg/l; pyridoxineHCl 0.50 mg/l; thiamine.HCl 1.0 mg/l; myo-inositol 100.0 mg/l; 2,4-D 1.5 mg/l; sucrose 20.0 g/l; glucose 10.0 g/l; L-proline 0.70 g/l; MES (Sigma) 0.50 g/l; 8.0 g/l agar (Sigma A-7049, purified) and 100 $\mu$M acetosyringone with a final pH of 5.8] for the PHI combined medium system. Any embryos left in the tube were transferred to the plate using a sterile spatula. The Agrobacterium suspension was drawn off and the embryos placed axis side down on the media. The plate was sealed with Parafilm tape or Pylon Vegetative Combine Tape (E. G. CUT; Kyowa Ltd., Japan) and incubated in the dark at 23–25° C. for about 3 days of co-cultivation.

For the resting step, all of the embryos were transferred to a new plate containing PHI-C medium [CHU(N6) basal salts (Sigma C-1416) 4.0 g/l; Eriksson's vitamin mix (1000× Sigma-1511) 1.0 ml/l; thiamine.HCl 0.5 mg/l; 2,4-D 1.5 mg/l; L-proline 0.69 g/l; sucrose 30.0 g/l; MES buffer (Sigma) 0.5 g/l; agar (Sigma A-7049, purified) 8.0 g/l; silver nitrate 0.85 mg/l; carbenicillin 100 mg/l; pH 5.8]. The plate was sealed with Parafilm or Pylon tape and incubated in the dark at 28° C. for 3–5 days.

For selection, all of the embryos were then transferred from the PHI-C medium to new plates containing PHI-D medium, as a selection medium, [CHU (N6) basal salts (SIGMA C-1416) 4.0 g/l; Eriksson's vitamin mix (1000×, Sigma-1511) 1.0 ml/l; thiamine.HCl 0.5 mg/l; 2,4-D 1.5 mg/l; L-proline 0.69 g/l; sucrose 30.0 g/l; MES buffer 0.5 g/l; agar (Sigma A-7049, purified) 8.0 g/l; silver nitrate 0.85 mg/l; carbenicillin (ICN, Costa Mesa, Calif.) 100 mg/l; bialaphos (Meiji Seika K.K., Tokyo, Japan) 1.5 mg/l for the first two weeks followed by 3 mg/l for the remainder of the time; pH 5.8] putting about 20 embryos onto each plate. The plates were sealed as described above and incubated in the dark at 28° C. for the first two weeks of selection. The embryos were transferred to fresh selection medium at two week intervals. The tissue was subcultured by transferring to fresh selection medium for a total of about 2 months. The herbicide-resistant calli were then "bulked up" by growing on the same medium for another two weeks until the diameter of the calli was about 1.5–2 cm.

For regeneration, the calli were then cultured on PHI-E medium [LMS salts 4.3 g/l; myo-inositol 0.1 g/l; nicotinic acid 0.5 mg/l, thiamine.HCl 0.1 mg/l, pyridoxine.HCl, 0.5 mg/l, glycine 2.0 mg/l, zeatin 0.5 mg/l, sucrose 60.0 g/l, agar (Sigma, A-7049) 8.0 g/l, indoleacetic acid (IAA, Sigma) 1.0 mg/l, abscisic acid (ABA, Sigma) 0.1 $\mu$M, Bialaphos 3 mg/l, carbenicillin 100 mg/l adjusted to pH 5.6] in the dark at 28° C. for 1–3 weeks to allow somatic embryos to mature. The calli were then cultured on PHI-F medium [MS salts 4.3 g/l; myo-inositol 0.1 g/l; thiamine.HCl 0.1 mg/l, pyridoxine.HCl 0.5 mg/l, glycine 2.0 mg/l nicotinic acid 0.5 mg/l; sucrose 40.0 g/l; Gelrite 1.5 g/l; pH 5.6] at 25° C. under a daylight schedule of 16 hours light (270 uE m$^{-2}$sec$^{-1}$) and 8 hours dark until shoots and roots developed. Each small plantlet was then transferred to a 25×150 mm tube containing PHI-F medium and grown under the same conditions for approximately another week. The plants were transplanted to pots with soil mixture in a greenhouse. Positive events were determined using methods similar to those used for examination of particle-bombarded transgenic maize at the callus stage or regenerated plant stage.

For Hi-II, a preferred optimized protocol used 0.5×10$^9$ cfu/ml Agrobacterium, a 3–5 day resting step, and no silver nitrate in the infection medium (PHI-A medium).

(b) Transformation of A188× Inbred Crosses Using the PHI Protocols

F$_1$ immature embryos were isolated from crosses of A188 to other inbreds and were subjected to transformation by Agrobacterium. The protocols used were essentially the same as outlined above, with the following modifications. The Agrobacterium suspension was prepared with either the N6 salt containing medium, PHI-G [100 ml/l of a 10× solution of N6 macronutrients (463.0 mg/l (NH$_4$)$_2$SO$_4$, 400.0 mg/l KH$_2$PO$_4$, 125.33 mg/l CaCl$_2$, 90.37 mg/l MgSO$_4$ and 2.830.0 mg/l KNO$_3$), 2.44 mg/l boric acid, 37.1 mg/l Na$_2$-EDTA.2H$_2$O, 27.88 mg/l FeSO4.7H$_2$O, 7.33 mg/l MnSO$_4$.H$_2$O, 0.77 mg/l KI, 0.6 mg/l ZnSO$_4$.7H$_2$O, 0.15 mg/l Na$_2$MoO$_2$.2H$_2$O, 1.68 g/l KNO$_3$, 0.8 mg/l glycine, 3.2 mg/l nicotinic acid, 3.2 mg/l pyridoxine.HCl, 3.4 mg/l thiamine.HCl, 0.6 g/l Myo-inositol, 0.8 mg/l 2,4-D, 1.2 mg/l Dicamba (Sigma), 1.98 g/l L-proline, 0.3 g/l casein hydrolysate, 68.5 g/l sucrose and 36.0 g/l glucose, pH 5.2] or the MS salt-containing medium, PHI-I (supra) for the infection step. The co-cultivation medium was PHI-J (supra) and the co-cultivation time was about 3 to about 7 days. For PHJ9O×A188, PHI-C medium (supra) was used in a 3 day resting step and PHI-D medium (supra) was used for selection. For PHN46×A188 and PHPP8×A188 transformations, no resting step was used, the co-cultivation time was about 5–7 days, and PHI-H medium [100 ml/l of a 10× solution of N6 macronutrients (463.0 mg/l (NH$_4$)$_2$SO$_4$, 400.0 mg/l KH$_2$PO$_4$, 125.33 mg/l CaCl$_2$, 90.37 mg/l MgSO$_4$ and 2,830 mg/l KNO$_3$), 2.44 mg/l boric acid, 37.1 mg/l Na$_2$-EDTA.2H$_2$O, 27.88 mg/l FeSO4.7H$_2$O, 7.33 mg/l MnSO$_4$.H$_2$O, 0.77 mg/l KI, 0.6 mg/l ZnSO$_4$.7H$_2$O, 0.15 mg/l Na$_2$MoO$_2$.2H$_2$O, 1.68 g/l KNO$_3$, 0.8 mg/l glycine, 3.2 mg/l nicotinic acid, 3.2 mg/l pyridoxine.HCl, 3.4 mg/l thiamine.HCl, 0.6 g/l Myo-inositol, 1.0 mg/l 2,4-D, 1.0 mg/l dicamba, 0.3 g/l casein hydrolysate, 20.0 g/l sucrose, 0.6 g/l glucose, 0.5 g/l MES buffer, 1 mg/l AgNO3, 5 mg/l bialaphos, 100 mg/l carbenicillin and 8.0 g/l Agar (Sigma A-7049, purified); pH 5.8] was used for selection. UDPGdH positive events were determined at the callus stage or could be determined at the regenerated plant stage.

EXAMPLE 4

OVER-EXPRESSION OF UDPGDH IN TRANSFORMFED CELLS (a) Expression Vector Construction The maize Zmudpgdh1 cDNA has a 1443 base pair open reading frame, which gives rise to a protein of 480 amino acids. To facilitate the cloning of this gene into a maize transformation vector, as well as into the pET vector, a RcaI site was introduced into the 5' end of the gene. There is an extra amino acid (threonine) positioned after the first methionine to keep the correct reading frame. Thus, the UDPGdH gene after the modification encodes a protein of 481 amino acids. The modified UDPGdH clone was inserted into the pCRII vector (Original TA Cloning® Kit; Invitro-Gen; Portland Oreg.), and the vector designated "PHI 11801."

(b) Analysis of UDPGdH Over-Expression

The RcaI/BamHI fragment of the UDPGdH clone (PHI 11801) was inserted into the pET28a vector digested with NcoI and BamHI. The pET28 vector was selected to obtain UDPGdH protein for the enzyme assay since pET28 adds no exogenous tags to aid in protein purification which might be inimical to enzyme function and activity determination. Two different cell lines, BL21 (DE3) and BL21 (DE3) pLysS, were used in these studies.

The time course and yield study showed that one hour after the IPTG induction, UDPGdH protein reached its peak in both cell lines. Growth after one hour (up to three hours) did not increase the proportional content of UDPGdH protein. The over-expressed UDPGdH represented about 40–50% of total protein in both cell lines. About 10% of the over-expressed UDPGdH protein appeared to be soluble in cell line BL21(DE3)pLysS, and about 5% appeared to be soluble in cell line BL21(DE3). Based on these results, BL21(DE3) pLysS was selected for further studies.

BL21(DE3)pLysS cells transformed with UDPGdH-pET28 were grown in 200 ml LB medium (50 $\mu$g/ml kanamycin). When the OD$_{600}$ reached 0.6, IPTG was added to final concentration of 0.4 mM. One hour after the IFTG induction, the cells were harvested by centrifugation at 5000×g for 5 minutes at 4° C. The pellet was resuspended in 5 ml of 50 mM Tris (pH 8.0) with a protease inhibitor cocktail (Boehinger Mannheim), and Triton X-100 was added to final concentration of 0.1%. One cycle of freeze-thaw was carried out to lyse the cells. Then, DNase was added (e.g., 200 units for a 200 ml culture, containing about one milligram of DNA) to digest the DNA for 20 minutes at room temperature. Since the suspension was still very viscous, DNA was sheared using a syringe. The suspension was centrifuged at 15,000 rpm (SS34 rotor) at 4° C. for 15 minutes. The supernatant was collected for UDPGdH enzymatic assay. In the assay, the negative control was prepared from the cell line BL21(DE3) pLysS transformed with pET28a (no insert).

The standard protocol for enzymatic assay of UDPGdH contains the following components in a final volume of 3.0 milliliters:

| Component | Volume added | Final concentration |
|---|---|---|
| 100 mM Glycine, pH 8.7 | 2.60 ml | 87 mM |
| 3 mM UDPG | 0.2 ml | 20 μM |
| 30 mM β-NAD | 0.1 ml | 1 mM |
| UDPGdH | 0.1 ml | 12.8 μg/ml |

The assay was performed by monitoring absorbance at 340 nm for 5 minutes. The results summarized in the table below present data for the enzyme produced in the E. coli over-expression system compared to a control that was made by transforming E. coli with vector having no UDPGdH gene insert. The table also includes UDPGdH enzyme purchased from Sigma Chemical Corporation, which is used as a positive control. The values for units/milliliter enzyme were calculated using the formula:

$$\frac{(dA340\,nm/min.\,for\,soluble\,extract) - (dA340\,nm/min.\,for\,negative\,control) \times 0.75 \times 1}{2 \times 6.229 \times (volume\,of\,extract)}$$

| | Rate (dA/min) | Total Protein | Units/ml | Units/mg |
|---|---|---|---|---|
| Blank | 0.000 | — | — | — |
| UDPGdH (Sigma) | 0.0214 | — | — | — |
| UDPGdH soluble extract | 0.0088 | 38.5 μg | 0.015 | 0.014 |
| Negative control | 0.0001 | 38.5 μg | — | — |

Although the foregoing refers to particular preferred embodiments, it will be understood that the present invention is not so limited It will occur to those of ordinary skill in the art that various modifications may be made to the disclosed embodiments and that such modifications are intended to be within the scope of the present invention, which is defined by the following claims.

We claim:

1. An isolated nucleic acid molecule comprising a polynucleotide encoding a UDP-glucose dehydrogenase (UDPGdH) polypeptide comprising an amino acid sequence of either SEQ ID NO:2 or SEQ ID NO:4.

2. The isolated nucleic acid molecule of claim 1 wherein the polypeptide has an amino acid sequence having at least 98% identity to the amino acid sequence of SEQ ID NO:2 or SEQ ID NO:4.

3. An isolated nucleic acid molecule encoding a UDPGDH polypeptide having at least 98% sequence identity to SEQ ID NOS: 1 or 3 or a full complement thereof.

4. The isolated nucleic acid molecule of claim 3 having the nucleotide sequence of either SEQ ID NO:1 or SEQ ID NO:3 or a full complement thereof.

5. An expression vector comprising a promoter that is operably linked with the nucleic acid molecule of claim 3.

6. A host cell comprising the expression vector of claim 5, wherein said host cell is selected from the group consisting of a bacterium, yeast cell, insect cell, and plant cell.

7. The host cell of claim 6, wherein said host cell is a plant cell selected from the group consisting of maize cell, sorghum cell, wheat cell, rice cell, barley cell, oat cell, and potato cell.

8. The host cell of claim 7, wherein said cell is a maize cell.

9. A transgenic plant comprising the expression vector of claim 5.

10. A transgenic plant comprising the expression vector of claim 5, wherein the cells of said transgenic plant express exogenous UDPGdH encoded by said expression vector, and wherein the total UDPGdH enzyme activity of said plant cells is greater than the UDPGdH enzyme activity of plant cells that do not express said exogenous UDPGdH.

11. The transgenic plant of claim 10, wherein said promoter is the 35S CaMV promoter.

* * * * *